United States Patent
Steemers et al.

(10) Patent No.: US 12,371,690 B2
(45) Date of Patent: *Jul. 29, 2025

(54) METHODS AND COMPOSITIONS USING ONE-SIDED TRANSPOSITION

(71) Applicant: Illumina, Inc., San Diego, CA (US)

(72) Inventors: Frank J. Steemers, Encinitas, CA (US); Jeffrey S. Fisher, San Diego, CA (US); Kevin L. Gunderson, San Diego, CA (US); Sasan Amini, Redwood City, CA (US); Christian Gloeckner, Bonn (DE)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/610,717

(22) Filed: Mar. 20, 2024

(65) Prior Publication Data

US 2024/0294904 A1    Sep. 5, 2024

Related U.S. Application Data

(60) Continuation of application No. 17/189,916, filed on Mar. 2, 2021, now Pat. No. 11,965,158, which is a continuation of application No. 16/736,043, filed on Jan. 7, 2020, now Pat. No. 10,968,448, which is a division of application No. 15/322,432, filed as application No. PCT/US2015/038050 on Jun. 26, 2015, now Pat. No. 10,577,603.

(60) Provisional application No. 62/019,209, filed on Jun. 30, 2014.

(51) Int. Cl.
*C12N 15/10* (2006.01)
*C12N 9/22* (2006.01)
*C12Q 1/6806* (2018.01)

(52) U.S. Cl.
CPC ........... *C12N 15/1093* (2013.01); *C12N 9/22* (2013.01); *C12Q 1/6806* (2013.01)

(58) Field of Classification Search
None
See application file for complete search history.

(56) References Cited

U.S. PATENT DOCUMENTS

| | | |
|---|---|---|
| 5,130,238 A | 7/1992 | Malek |
| 5,185,243 A | 2/1993 | Ullman |
| 5,223,414 A | 6/1993 | Zarling |
| 5,455,166 A | 10/1995 | Walker |
| 5,573,907 A | 11/1996 | Carrino |
| 5,599,675 A | 2/1997 | Brenner |
| 5,641,658 A | 6/1997 | Adams |
| 5,679,524 A | 10/1997 | Nikiforov |
| 5,750,341 A | 5/1998 | Macevicz |
| 5,925,545 A | 7/1999 | Reznikoff |
| 5,965,443 A | 10/1999 | Reznikoff |
| 6,210,891 B1 | 4/2001 | Nyren |
| 6,258,568 B1 | 7/2001 | Nyren |
| 6,274,320 B1 | 8/2001 | Rothberg |
| 6,437,109 B1 | 8/2002 | Reznikoff et al. |
| 6,593,113 B1 | 7/2003 | Tenkanen et al. |
| 7,001,792 B2 | 2/2006 | Sauer |
| 7,057,026 B2 | 6/2006 | Barnes |
| 7,083,980 B2 | 8/2006 | Reznikoff |
| 7,115,400 B1 | 10/2006 | Adessi |
| 7,138,267 B1 | 11/2006 | Jendrisak et al. |
| 7,211,414 B2 | 5/2007 | Hardin |
| 7,244,559 B2 | 7/2007 | Rothberg |
| 7,315,019 B2 | 1/2008 | Turner |
| 7,329,492 B2 | 2/2008 | Hardin |
| 7,399,590 B2 | 7/2008 | Piepenburn |
| 7,405,281 B2 | 7/2008 | Xu |
| 7,537,897 B2 | 5/2009 | Brenner et al. |
| 7,582,420 B2 | 9/2009 | Oliphant |
| 7,595,883 B1 | 9/2009 | Gamal |
| 7,608,434 B2 | 10/2009 | Reznikoff |
| 7,611,869 B2 | 11/2009 | Fan |
| 7,670,810 B2 | 3/2010 | Gunderson |
| 2002/0055100 A1 | 5/2002 | Kawashima |
| 2004/0002090 A1 | 1/2004 | Mayer |
| 2004/0096853 A1 | 5/2004 | Mayer |
| 2004/0110191 A1 | 6/2004 | Winkler et al. |
| 2005/0191698 A1 | 9/2005 | Chee |
| 2006/0024681 A1 | 2/2006 | Smith et al. |
| 2006/0216309 A1 | 9/2006 | Holden |
| 2007/0128610 A1 | 6/2007 | Buzby |
| 2007/0128624 A1 | 6/2007 | Gormley |

(Continued)

FOREIGN PATENT DOCUMENTS

| | | |
|---|---|---|
| EP | 0320308 | 6/1989 |
| EP | 0336731 | 10/1989 |

(Continued)

OTHER PUBLICATIONS

Bains et al., A Novel Method for Nucleic Acid Sequence Determination, Journal of Theoretical Biology 135(3), 303-7 (1988).
Bentley et al., Accurate Whole Human Genome Sequencing using Reversible Terminator Chemistry Nature 456:53-59 (2008).
Boeke, et al., Transcription and Reverse Transcription of Retrotransposons, Annu Rev Microbiol. 43:403-34 (1989).
Brown, et al., Retroviral integration: Structure of the initial covalent product and its precursor, and the role for the viral IN protein, Proc Natl Acad Sci USA, 86:2525-9 (1989)
Cockroft et al., A single-molecule nanopore device detects DNA polymerase activity with single-nucleotide resolution, J. Am. Chem. Soc. 130:818-820 (2008).

(Continued)

*Primary Examiner* — Christopher M Gross
(74) *Attorney, Agent, or Firm* — Illumina, Inc.

(57) ABSTRACT

Embodiments provided herein relate to methods and compositions for next generation sequencing. Some embodiments include the preparation of a template library from a target nucleic acid using one-sided transposition, sequencing the template library, and capturing the contiguity information.

20 Claims, 16 Drawing Sheets

(56) References Cited

U.S. PATENT DOCUMENTS

| | | |
|---|---|---|
| 2008/0009420 A1 | 1/2008 | Schroth |
| 2008/0108082 A1 | 5/2008 | Rank |
| 2009/0026082 A1 | 1/2009 | Rothberg |
| 2009/0047680 A1 | 2/2009 | Lok |
| 2009/0127589 A1 | 5/2009 | Rothberg |
| 2010/0022403 A1 | 1/2010 | Kurn |
| 2010/0069263 A1 | 3/2010 | Shendure et al. |
| 2010/0111768 A1 | 5/2010 | Banerjee |
| 2010/0120098 A1 | 5/2010 | Grunenwald et al. |
| 2010/0137143 A1 | 6/2010 | Rothberg |
| 2010/0282617 A1 | 11/2010 | Rothberg |
| 2011/0014657 A1 | 1/2011 | Rigatti |
| 2011/0059865 A1 | 5/2011 | Smith |
| 2011/0311506 A1 | 12/2011 | Lynn et al. |
| 2012/0053063 A1 | 3/2012 | Rigatti et al. |
| 2012/0208705 A1 | 8/2012 | Steemers |
| 2012/0208724 A1 | 8/2012 | Steemers |
| 2012/0270305 A1 | 10/2012 | Reed |
| 2012/0282617 A1 | 11/2012 | Mao |
| 2012/0301925 A1 | 11/2012 | Belyaev |
| 2013/0017978 A1 | 1/2013 | Kavanagh |
| 2014/0079923 A1 | 3/2014 | George |
| 2014/0093916 A1 | 4/2014 | Belyaev |
| 2014/0194324 A1 | 7/2014 | Gormley |
| 2015/0159212 A1* | 6/2015 | Pantoja .............. C12N 15/1065 506/26 |
| 2015/0291942 A1 | 10/2015 | Gloeckner |

FOREIGN PATENT DOCUMENTS

| | | |
|---|---|---|
| EP | 0439182 | 7/1991 |
| EP | 2712931 A1 | 4/2014 |
| WO | WO 1989/09835 | 10/1989 |
| WO | WO 1989/10977 | 11/1989 |
| WO | WO 1989/012696 | 12/1989 |
| WO | WO 1990/01069 | 2/1990 |
| WO | WO 1991/006678 | 5/1991 |
| WO | WO 1995/023875 | 9/1995 |
| WO | 1998044151 A1 | 10/1998 |
| WO | WO 2004/018497 | 3/2004 |
| WO | WO 2005/065814 | 7/2005 |
| WO | 2005100585 A2 | 10/2005 |
| WO | 2007098279 A2 | 8/2007 |
| WO | WO 2007/123744 | 11/2007 |
| WO | WO 2010/048605 | 4/2010 |
| WO | WO 2012/025250 | 3/2012 |
| WO | WO 2012/058096 | 5/2012 |
| WO | WO 2012/061832 | 5/2012 |
| WO | 2012106546 A2 | 8/2012 |
| WO | WO 2012/103545 | 8/2012 |
| WO | WO 2014/018423 | 1/2014 |
| WO | WO 2014/142850 | 9/2014 |

OTHER PUBLICATIONS

Colegio et al., In vitro transposition system for efficient generation of random mutants of campylobacter jejuni, J. Bacteriol., 183: 2384-8 (2001).

Craig, Transposon Tn7, Curr Top Microbiol Immunol., 204:27-48 (1996).

Craig, V(D)J Recombination and Transposition: Closer than Expected, Science 271:1512 (1996).

Deamer, et al, Nanopores and nucleic acids: prosepects for ultrarapid sequencing, Trends Biotechnol. 18, 147-151 (2000).

Deamer, et al Characterization of nucleic acids by nanopore analysis, Acc. Chem. Res. 35:817-825 (2002).

Dean et al., Comprehensive human genome amplification using multiple displacement amplification, Proc. Natl. Acad. Sci. USA 99:5261-66 (2002).

Devine et al, Efficient integration of artificial transposons into plasmid targets in vitro: a useful tool for DNA mapping, sequencing and genetic analysis, Nucleic Acids Res., 22: 3765-72 (1994).

Drmanac et al., Accurate sequencing by hybridization for DNA diagnostics and individual geonomics, Nature Biotechnology 16:54-58 (1998).

Fodor et al., Light-Directed, Spatially Addressable Parallel Chemical Synthesis, Science 251(4995), 767-773 (1995).

Gloor, Gene Targeting in *Drosophila*, Methods Mol. Biol., 260: 97-114 (2004).

Goryshin et al, Tn5 in vitro transposition, J. Biol. Chem., 273:7367-7374 (1998).

Haapa S., et al., An efficient and accurate integration of mini-Mu transposons in vitro: a general methodology for functional genetic analysis and molecular biology applications, N.A. Res. 27:2777-2784 (1999).

Healy, Nanopore-based single-molecule DNA analysis, Nanomed. 2:459-481 (2007).

Ichikawa, et al, In Vitro Transposition of Transposon Tn3*, J Biol. Chem. 265: 18829-32 (1990).

Joos et al., Covalent Attachment of Hybridizable Oligonucleotides to Glass Supports, Anal Biochem, 247:96-101 (1997).

Khandjian, UV Crosslinking of RNA to Nylon Membrane Enhances Hybridization Signals, Mol. Bio. Rep., 11:107-11 (1986).

Kirby et al., Cryptic plasmids of *Mycobacterium avium*: Tn552 to the rescue, Mol. Microbiol., 43: 173-86 (2002).

Kleckner et al., Tn10 and IS10 Transposition and Chromosome Rearrangements: Mechanism and Regulation In Vivo and In Vitro, Curr Top Microbiol Immunol. 204:49-82 (1996).

Korlach et al. Selective aluminum passivation for targeted immobilization of single DNA polymerase molecules in zero-mode waveguide nanostructures, Proc. Natl. Acad. Sci. USA 105, 1176-1181 (2008).

Lage et al., Whole genome analysis of genetic alterations in small DNA samples using hyperbranched strand displacement amplification and array—CGH, Genome Research 13:294-307 (2003).

Lampe et al., A purified mariner transposase is sufficient to mediate transposition in vitro, EMBO J., 15: 5470-9 (1996).

Leschzinger, et al, Tn552 transposase catalyzes concerted strand transfer in vitro, Proc Nat Acad Sci 95:7345-7350 (1998).

Levene et al., Zero-mode waveguides for single-molecule analysis at high concentrations, Science 299, 682-686 (2003).

Li et al., DNA molecules and configurations in a solid-state nanopore microscope, Nat. Mater. 2:611-615 (2003).

Lisch, Damon, How important are transposons for plant evolution? Nature Reviews 14:49-61 (2013).

Lundquist et al. Parallel confocal detection of single molecules in real time, Opt. Lett. 33:1026-1028 (2008).

Marine, et al, Evaluation of a transposase protocol for rapid generation of shotgun high-throughput sequencing libraries from nanogram quantities of DNA, Applied Environ Microbiology 77(22):8071-8079 (2011).

Mizuuchi, In Vitro Transposition of Bateriophage Mu: A Biochemical Approach to a Novel Replication Reaction, Cell 35:785-794 (1983).

Ohtsubo et al, Bacterial Insertion Sequences, Curr Top. Microbiol. Immunol. 204: 1-26 (1996).

Oroskar et al., Detection of immobilized amplicons by ELISA-like techniques, Clin. Chem. 42:1547-1555 (1996).

Picelli, et al, Full-length RNA-seq from single cells using Smart-seq2, Nature Protocols 9(1):171-181 (2014).

Plasterk, The Tc1/mariner Transposon Family, Curr Topics Microbiol. Immunol., 204: 125-143 (1996).

Rasila TS, et al., Flexibility in MuA Transposase Family Protein Structures: Functional Mapping with Scanning Mutagenesis and Sequence Alighment of Protein Homologues, (2012) PLoS ONE 7(5):e37922. doi:10.1371/journal.pone.0037922.

Richardson et al., Mechanism of Mos1 transposition: insights from structural analysis, EMBO Journal 25:1324-1334 (2006).

Ronaghi et al. DNA Sequencing: A Sequencing Method Based on Real-Time Pyrophosphate, Science 281(5375):363-365 (1998).

Ronaghi, et al., Real-time DNA sequencing using detection of pyrophosphate release, Analytical Biochemistry 242(1): 84-89 (1996).

Ronaghi, Pyrosequencing sheds light on DNA sequencing, Genome Res. 11(1): 3-11 (2001).

(56) References Cited

OTHER PUBLICATIONS

Savilahti, et al., The phage Mu transpososome core: DNA requirements for assembly and function, EMBO J. 14: 4893 15 (1995).
Shendure et al. Accurate multiplex polony sequencing of an evolved bacterial genome, Science 309:1728-1732 (2005).
Smith et al., Direct Mechanical Measurements of the Elasticity of Singe DNA Molecules by Using Magnetic Beads, Science, 258:1122-1126 (1992).
Soni et al, Progress toward ultrafast DNA sequencing using solid-state nanopores, Clin. Chem. 53: 1996-2001 (2007).
Taylor et al. Characterization of chemisorbed monolayers by surface potential measurements, J. Phys. D: Appl. Phys., 24:1443-1450 (1991).
Walker et al., Molecular Methods for Virus Detection, Academic Press, Inc., 1995.
Walker et al., Stand displacement amplification—an isothermal, in vitro DNA amplification technique, Nucl. Acids Res. 20:1691-96 (1992).
Wilson et al., New transposon delivery plasmids for insertional metagenesis in Bacillus anthracis, Microbiol. Methods 71:332-5 (2007).
Xu et al., Helicase-dependent isothermal DNA amplification, EMBO Rep 5:795-800 (2004).
Zhang et al., A novel mechanism of transposon-mediated gene activation, PLoS Genet. 5:e1000689. Epub Oct. 16, 2009.
Adey et al., "Rapid, low-input, low-bias construction of shotgun fragment libraries by high-density in vitro transposition," Genome Biology, 2010, pp. 1-17.
Adey et al., "Ultra-low-input, tagmentation-based whole-genome bisulfite sequencing," Cold Spring Harbor Laboratory Press, Mar. 30, 2012, pp. 1139-1143.
Bimber et al., "Whole-genome characterization of human and simian immunodeficiency virus intrahost diversity by uptradeep pyrosequencing," Journal of Virology, vol. 84, No. 22, 2010, pp. 12087-12092.
Bloch et al., "Purification of *Escherichia coli* chromosomal segements without cloning," Biochemical and Biophysical Research Communications, vol. 223, 1996, pp. 104-111.
Brownlie et al., "The Caenorhabditis briggsae genome contains active CbmaT1 and Tcb1 transposons," Molecular Genetics and Genomics, vol. 273, 2005, pp. 92-101.
Chernoff et al., "Molecular Analysis of the von Hippel-Lindau Disesase Gene," Methods. Mol. Med. 53, 2001, pp. 193-216.
Cokus et al., "Shotgun bisulphite sequencing of the *Arabidopsis* genome reveals DNA methylation patterning," Nature 452(7184), 2008, pp. 215-219.
De Vries et al., "PCR on Cell Lysates Obtained from Whole Blood Circumvents DNA Isloation," Clin. Chem. 47, 2001.
Fullwood et al., "Chromatin interaction analysis using paired-end tag sequencing," Current Protocols in Molecular Biology, Supplement, 89, 2010, pp. 21.15.1-21.15.25.
Gal et al., "Directional cloning of native PCR products with preformed sticky ends (autosticky PCR)," Molecular & General Genetics, vol. 260, No. 6, 1999, pp. 569-573.
Goodman et al., "Identifying genetic determinants needed to establish a human gut symbiont in its habit," Cell Host & Microbe, vol. 6, Sep. 2009, pp. 279-289.
Grunenwald et al., "Rapid, high-throughput library preparation for next-generation sequencing, Nature Methods, Application Notes," Nature Methods, Aug. 2010, pp. iii-iv.
Heredia et al., "In vitro double transposition for DNA identification," Analytical Biochemistry 399, 2010, pp. 78-83.
Jackson et al., "Plasmid tagging for efficient large-scale sequence completion of entire clone inserts," BioTechniques, vol. 34, Mar. 2003, pp. 604-608.
Kirby, "In vivo mutagenesis using EZ-Tn5TM," Methods in Enzymology, vol. 421, 2007, pp. 17-21.
Kitzman et al., "Haplotype-resolved genome sequencing of a Guajarati Indian individual," Nature Biotechnology, Jan. 2011, pp. 5963.
Kramer, "cDNA Library Construction from Single Cells," Current Protocols in Neuroscience, 2002, pp. 4.27.1-4.27.19.
McCloskey et al., "Encoding PCR Products with Batch-stamps and Barcodes," Biochem Genet 45, 2007, pp. 761-767.
Miner et al., "Molecular barcodes detect redundancy and contamination in hairpin-bisulfite PCR," Nucleic Acids Research, 2004, vol. 32, No. 17, Sep. 30, 2004, 4 pages.
Nijman et al., "Mutation discovery by targeted genomic enrichment of multiplexed barcoded samples," Nature Methods, vol. 7, No. 11, 2021, pp. 913-915.
Oh et al., "A universal TagModule collection for parallel genetic analysis of microorganisms," Nucleic Acids Research, vol. 38, No. 14, May 21, 2010, p. 146.
Oh, "A Robust Platform for High-Throughput Genomics in Microorganisms," A dissertation submitted to the department of genetics and the committee on graduate studies of Stanford University in partial fulfillment of the requirements for the degree of doctor of philosophy, Mar. 2010, pp. i, ii, 10-30.
Ooka et al., "Inference of the impact of insertion sequence (IS) elements on bacterial genome diversification through analysis of small-size structural polymorphisms in *Escherichia coli* O157 genomes," 2009, Genome Research, vol. 19, 2009, pp. 1809-1816.
Pobigaylo et al., "Construction of a large signature-tagged minOTn5 transposon library and its application to mutagenesis of Sinorhizobium meliloti," Applied and Environmental Microbiology, vol. 72, No. 6, Jun. 2006, pp. 4329-4337.
Schwartz et al., "Capturing native long-range contiguity by in situ library construction and optical sequencing," Proceedings of the National Academy of Sciences, 2012, pp. 18749-18754.
Shevchenko et al., "Systematic sequencing of cDNA clones using the transposon Tn5," Nucl. Acids Res. 30, 2002, pp. 2469-2477.
Syed et al., "Optimized library preparation method for next-generation sequencing," Nature Methods, 6(10), Oct. 1, 2009, pp. I-II.
Wang et al., "Calling Cards Enable Multiplexed Identification of the Genomic Targets of DNA-binding Proteins," Genome Research, May 1, 2011, pp. 748-755.
Xu, Extracting Haplotypes from Diploid Organisms, Current Issues in Molecular Biology, vol. 8, Jul. 2006, pp. 113-122.
Zeevi et al., "Increasing cloning possibilities using artificial zinc finger nucleases," Proceedings of the National Academy of Sciences, USA, vol. 105, Nov. 35, Sep. 2008, pp. 12785-12790.
Zhou et al., "Molecular genetic analysis of tarnsposase-end DNA sequence recognition: Cooperativity of three adjacent base-pairs in specific interaction with a mutant Tn5 transposase," Journal of Molecular Biology, vol. 276, 1998, pp. 913-925.

\* cited by examiner

METHODS AND COMPOSITIONS USING ONE-SIDED TRANSPOSITION

RELATED APPLICATION

This application is a continuation of U.S. application Ser. No. 17/189,916 filed Mar. 2, 2021 which is a continuation of U.S. application Ser. No. 16/736,043 filed Jan. 7, 2020, now U.S. Pat. No. 10,968,448 issued Apr. 6, 2021 which is a division of U.S. application Ser. No. 15/322,432 filed Dec. 27, 2016, now U.S. Pat. No. 10,577,603 issued Mar. 3, 2020 which is the U.S. national phase entry of PCT Application No. PCT/US2015/038050 filed Jun. 26, 2015 which was published in English as WO 2016/003814 on Jan. 7, 2016 which claims priority to U.S. Prov. App. No. 62/019,209 filed on Jun. 30, 2014 which are each incorporated by reference in its entirety.

FIELD OF THE INVENTION

Embodiments provided herein relate to methods and compositions for next generation sequencing. Some embodiments include the preparation of a template library from a target nucleic acid using one-sided transposition, also known as one sided transposition, sequencing the template library, and capturing contiguity information.

BACKGROUND OF THE INVENTION

Several next generation sequencing technologies are available for fast and economical determination of a genome's entire sequence. Typically, a library of template nucleic acids is prepared from a target genomic DNA sample prior to sequencing. The sample preparation usually includes a DNA fragmentation step that breaks the larger DNA strands into smaller DNA fragments that are more amenable to next generation sequencing technologies. Oftentimes adaptors are attached to the ends of the DNA fragments, which can be accomplished by DNA end repair followed by adaptor ligation, or more recently by using a transposome system. The use of transposomes, which is a complex of a transposase and transposon nucleic acids, allows for simultaneous genomic fragmentation and adaptor ligation of fragments thereby simplifying library preparation. However, fragmentation of genomic DNA can lead to a loss in information with regards to individual nucleic acid molecules for contiguity, phasing and haplotype. Therefore, a need exists for alternative library preparation methods.

SUMMARY OF THE INVENTION

In some embodiments described herein are methods for one-sided transposition. Inventors of this present application has surprisingly found that by performing one sided transposition, the double stranded target DNA is nicked at one strand only and the target DNA after such transposition remains intact even after the transposomes are removed. Thus, the contiguity of the target DNA is maintained ever after the transposition event. In some embodiments, methods for one-sided transposition can be used for capturing contiguity information. In some embodiments, methods for one-sided transposition can be used for preparing a sequencing library. In some embodiments, methods for one-sided transposition can be used for determining the phasing information or haplotype information.

In some embodiments, a transposome dimer is configured to nick only one strand of the double stranded target DNA and transfer only one transferred strand of the transposon of a transposome monomer to the nicked target DNA. In some embodiments, one monomer unit of a transposome dimer is incapable of transposition resulting in one-sided transposition. In some embodiments, one transposase of a transposome dimer can form the transposome complex by binding to the transposon, but incapable of nicking the target DNA.

In some embodiments, the transposon is functional such that transposomes are formed by contacting the transposons to the transposases and the transposon sequence can be transferred to target nucleic acid. In some embodiments, the transposon is non-functional such that transposomes are formed by contacting the transposons to the transposases but the transposon sequence cannot be transferred to target nucleic acid. In some embodiments, the 3'-end of the transferred strand comprise a 3'-terminal nucleic acid that is incapable of a nucleophilic attack on the 5'-end of the target nucleic acid. In some embodiments, the 3'-end of the recognition sequence is blocked. In some embodiments, the 3'-end of the blocked recognition sequence comprise a 3'-terminal dideoxy nucleotide, an amine group, alkyl group, aryl group, thiol group, a sulfate group, reverse nucleotide, an azido group, or a biotin.

In some embodiments, the transposase is capable of forming transposome but incapable of nicking the target DNA. In some embodiments, the transposase comprise one or more amino acid modifications such that it is capable of forming transposome but incapable of nicking a target DNA.

In some embodiments, the transposome complex is configured in such a way that the transposome is incapable of forming a dimer efficiently. In some embodiments, the transposome complex is configured in such a way that the transposome is incapable of forming a dimer at all. In some embodiments, the transposome monomer forms a nick in one strand of the double stranded DNA only and transfer the transferred strand of the transposon to the nicked target DNA.

In some embodiments, the one-sided transposition is performed by exploiting the differential resistance to transposition by the two strands of target DNA. In some embodiments, one strand of the target DNA comprises modified bases or modified phosphodiester bonds that are resistant to transposition. Exposing a target DNA having differential resistance to transposition by the two strands of target DNA to transposomes result in one-sided transposition. In some embodiments, the target nucleic acid is a double stranded cDNA in which one strand of the cDNA comprises modified bases and/or modified phosphodiester bonds such that that strand is resistant to transposition. In some embodiments, the target nucleic acid is a double stranded genomic DNA in which one strand is modified in a manner such that that strand is partially or totally resistant to transposition.

An exemplary one-sided transposition scheme is shown in FIG. 14. In some embodiments, starting with a single-stranded nucleic acid template (solid line), a complementary strand (dotted line) is synthesized which has a differential resistance to transposition than the original template strand. Then using even normal transposon complexes (e.g. active and unblocked), single-sided transposition occurs. In one example, the newly synthesized strand has a higher resistance to transposition. In another example, the original template is highly resistant, and the synthesized strand allowing transposition into itself. In this embodiment, the less resistant strand forms the library elements, which are held in contiguity by the more resistant strand.

Applicant surprisingly found that after carrying out one-sided transposition, the double stranded target nucleic acid remains intact without losing the contiguity information even after removing the transposase of the transposome. In some embodiments, the transposases are removed from the transposed target nucleic acid after transposition by the treatment with SDS, urea, protease, or heat. Accordingly, one sided transposition can be advantageous for determining sequence information, contiguity information, phasing information, and haplotype information. Contiguity information may provide extensive haplotype resolving power. Haplotyping allows for phasing of rare alleles and structural variants such as gene rearrangements, gene duplication.

In some embodiments, one-sided transposition can be coupled with combinatorial barcoding in which the first sets of barcodes are attached via one-sided transposition and the second set of barcodes are attached by subsequent amplification.

In some embodiments, the first sets of barcodes are introduced to the target nucleic acid during transposition to generate transposed target nucleic acid comprising first set of barcodes. The transposed target nucleic acids are pooled to generate a first pool of transposed target nucleic acid. A second set of barcodes are introduced to the first pool of transposed target nucleic acids to generate target nucleic acid comprising first and second sets of barcodes. The second set of barcodes may be introduced either by subsequent amplification, ligation, or additional transposition. In some embodiments, the first and second set of barcodes is different. The target nucleic acid comprising first and second sets of barcodes; are pooled to generate a second pool of transposed target nucleic acid. Optionally the steps of introducing additional barcodes and pooling to generate a library of barcoded target nucleic acids may be repeated.

In some embodiments, one-sided transposition can be used for determining the sequence information or contiguity information of nucleic acid from single cells. The nucleic acid can be genomic nucleic acid or cDNA generated from the mRNA of the single cell. In some embodiments, a first set of barcodes may be introduced to the nucleic acid from single cells that serve as an identifier of the single cell. In some embodiments, after introducing the first set of barcodes to the nucleic acid from single cells, the barcoded nucleic acid can be pooled and further processed by subsequent amplification, ligation, or additional transposition with or without introducing additional barcodes.

Some embodiments of the methods and compositions provided herein include a method of preparing a sequencing library from a double-stranded target nucleic acid comprising: (a) providing a plurality of transposomes, each transposome comprising a transposase and a transposon nucleic acid in which the transposome is configured to nick and transfer the transposon to only one strand of the target nucleic acid; and (b) contacting the target nucleic acid with the transposomes such that the target nucleic acid is nicked at a plurality of sites of the target nucleic acid and transposon nucleic acids are attached to the nicked target nucleic acid, thereby obtaining a library of modified nucleic acids for sequencing.

Some embodiments include a method of preparing a sequencing library from a double-stranded target nucleic acid comprising: (a) providing a plurality of transposomes, each transposome comprising a transposase and a transposon nucleic acid in which the transposome is configured to nick and transfer the transposon to only one strand of the target nucleic acid; (b) contacting the target nucleic acid with the transposomes such that the target nucleic acid is nicked at a plurality of sites of the target nucleic acid and transposon nucleic acids are attached to the nicked target nucleic acid; and (c) hybridizing primers to the transposon nucleic acids and extending the hybridized primers, thereby obtaining library of modified nucleic acids for sequencing. Exemplary schemes of library preparation using one sided transposition are shown in FIG. 13.

Some embodiments include a method for capturing contiguity information of a target DNA. The method includes (a) providing a plurality of transposomes, each transposome monomer comprising a transposase and a transposon nucleic acid in which the transposome is configured to nick only one strand of the double stranded target nucleic acid; (b) contacting the target DNA with the transposomes such that the target DNA is nicked at a plurality of sites of the target nucleic acid; (c) adding or inserting one or more recognition sequences to the target DNA sequence to generate treated target DNA; (d) sequencing the treated target DNA; and (e) capturing contiguity information by identifying the target DNA sequences or recognition sequences having a shared property.

Some embodiments include a method of capturing contiguity information of a target DNA. The method includes (a) providing a plurality of transposomes, each transposome monomer comprising a transposase and a transposon nucleic acid comprising a recognition sequence, wherein the transposome is configured to nick only one strand of the double stranded target nucleic acid; (b) inserting the transposon nucleic acids into strands of the target nucleic acid, comprising: (i) contacting the target nucleic acid with the transposomes such that the target nucleic acid is nicked at a plurality of sites and single transposon nucleic acids are attached to the nicked strands at one side of the nicked sites, and (ii) ligating the attached single transposon nucleic acids to the nicked strands at the other side of the nicked sites, thereby obtaining a modified nucleic acid; (c) amplifying the modified nucleic acid, thereby obtaining a plurality of nucleic acids comprising inserted recognition sequences; (d) sequencing the treated target DNA; and (e) capturing contiguity information by identifying the target DNA sequences or recognition sequences having a shared property.

Some embodiments also include capturing the modified nucleic acids on a surface.

In some embodiments, the transposomes that are contacted with the target nucleic acids in (b) are attached to a surface, thereby capturing the modified nucleic acids on the surface.

Some embodiments also include sequencing the captured nucleic acids on the surface.

In some embodiments, the proximity of sequence information obtained from two captured nucleic acids in a linear representation of the target nucleic acid sequence is indicative of the proximity of the captured nucleic acids on the surface.

In some embodiments, captured nucleic acids in closer proximity to one another on the surface comprise sequences in closer proximity in the representation of the target nucleic acid sequence compared to captured nucleic acids in less close proximity.

In some embodiments, the representation of the target nucleic acid sequence comprises a haplotype representation. In some embodiments, the representation of the target nucleic acid sequences comprises ordered short reads.

In some embodiments, the transposase comprises a one-sided transposase activity.

In some embodiments, the transposase comprises a monomer subunit lacking transposase activity. In some embodiments, the transposase comprises covalently linked monomer subunits. In some embodiments, the quaternary structure of the transposase is monomeric. In some embodiments, the transposase lacks the ability to form dimers.

In some embodiments, the transposase is selected from the group consisting of Mu, Mu E392Q, Tn5, hyperactive Tn5 (Goryshin and Reznikoff, J. Biol. Chem., 273:7367 (1998)), EZ-Tn5™ Transposase (Epicentre Biotechnologies, Madison, Wisconsin), variants of Tn5, RAG, Tn7, Tn10, Vibhar transposase, and Tn552. Variants of Tn5 transposases, such as having amino acid substitutions, insertions, deletions, and/or fusions with other proteins or peptides are disclosed in U.S. Pat. Nos. 5,925,545; 5,965,443; 7,083,980; 7,608,434; and U.S. patent application Ser. No. 14/686,961. The patents and the patent application are incorporated herein by reference in its entirety. In some embodiments, the Tn5 transposase comprise one or more substitutions at positions 54, 56, 372, 212, 214, 251, and 338 with respect to the wild type protein as disclosed in U.S. patent application Ser. No. 14/686,961. In some embodiments, the Tn5 wild-type protein or its variant can further comprise a fusion polypeptide. In some embodiments, the polypeptide domain fused to the transposase can comprise, for example, Elongation Factor Ts. Each of the references cited in this paragraph is incorporated herein by reference in its entirety.

In some embodiments, the transposon nucleic acid is blocked. In some embodiments, the 3'-end of the transferred strand of the transposon is blocked. In some embodiments, the 3' end of the blocked transposon nucleic acid is selected from the group consisting of a dideoxy group, a spacer group, an amine group, an azido group, a phosphate group, alkyl group, reverse nucleotide, and a biotin group. In some embodiments, transposon sequence can be altered by substitution, addition or deletion of bases from the transposon sequence.

In some embodiments, the plurality of transposomes is prepared by contacting the transposases with functional transposon nucleic acids and non-functional transposon nucleic acids. In some embodiments, the non-functional transposon comprises blocked transposon. In some embodiments, the ratio of transposon nucleic acids comprising non-functional transposon nucleic acids to functional transposon nucleic acids is greater than or equal to 1:1 In some embodiments, the ratio of transposon nucleic acids comprising non-functional transposon nucleic acids to functional transposon nucleic acids can be 1:2, 1:3, 1:5, 1:10, 1:20, 1:30, 1:40, 1:50, 1:75, 1:100, 2:1, 3:1, 4:1, 5:1, 6:1, 7:1, 8:1, 9:1, 10:1, 20:1, 30:1, 40:1, 50:1, 60:1, 70:1, 80:1, 90:1, or 100:1.

Some embodiments also include amplifying the extended nucleic acids. In some embodiments, amplifying the extended nucleic acids is with tailed amplification primers comprising a sequence selected from the group consisting of an anchor site, a sequencing primer site, an amplification primer site, and a reporter tag.

Some embodiments also include amplifying the captured nucleic acids. In some embodiments, amplifying of the captured nucleic acids comprises bridge amplification.

In some embodiments, the surface comprises a plurality of capture probes. In some embodiments, the capture probes comprise nucleic acids. Some embodiments also include hybridizing the modified nucleic acids with the capture probes.

In some embodiments, the modified nucleic acids and the capture probes each comprise an affinity moiety. In some embodiments, affinity moieties can be members of a binding pair. In some cases, the modified nucleic acids may comprise a first member of a binding pair and the capture probe may comprise a second member of the binding pair. In some cases, capture probes may be immobilized to a solid surface and the modified nucleic acid may comprise a first member of a binding pair and the capture probe may comprise a second member of the binding pair. In such cases, binding the first and second members of the binding pair immobilizes the modified nucleic acid to the solid surface. Examples of binding pair include but are not limited to biotin-avidin, biotin-streptavidin, biotin-neutravidin, ligand-receptor, hormone-receptor, lectin-glycoprotein, and antigen-antibody.

Some embodiments also include binding the affinity moiety of the modified nucleic acids with the affinity moiety of the capture probes.

In some embodiments, the transposon nucleic acid comprises a sequence selected from the group consisting of an anchor site, a barcode, a sequencing primer site, an amplification primer site, a unique molecular index, and a reporter tag.

In some embodiments, at least one transposome comprises two transposon nucleic acids.

In some embodiments, the two transposon nucleic acids have different sequences.

In some embodiments, the plurality of transposomes comprises at least two different transposon nucleic acids.

In some embodiments, the target nucleic acid is selected from the group consisting of DNA and RNA. In some embodiments, the target nucleic acid is selected from the group consisting of genomic DNA and cDNA. In some embodiments, the target nucleic acid is genomic DNA.

In some embodiments, the surface is on a substrate selected from the group consisting of a bead, slide, flow cell, channel, dip-stick, and well.

In some embodiments, the surface comprises at least about 10,000 captured nucleic acids per $mm^2$. In some embodiments, the surface comprises at least about 100,000 captured nucleic acids per $mm^2$. In some embodiments, the surface comprises at least about 1,000,000, 1,500,000, 2,000,000, 3,000,000, 5,000,000, 10,000,000, 15,000,000, 20,000,000, 30,000,000, 40,000,000, 50,000,000, 60,000,000, 70,000,000, 80,000,000, 90,000,000, 100,000,000, 150,000,000, 200,000,000, 300,000,000, 350,000,000, 400,000,000, 450,000,000, 500,000,000, 550,000,000, 600,000,000, 650,000,000, 700,000,000, 750,000,000, 800,000,000, 850,000,000, 900,000,000, 950,000,000, 1000,000,000, 1200,000,000, 1300,000,000, 1400,000,000, 1500,000,000, 1600,000,000, 1700,000,000, 1800,000,000, 1900,000,000, 2000,000,000, 3000,000,000, 4000,000,000, 5000,000,000, 6000,000,000, 7000,000,000, 8000,000,000, 9000,000,000, 10,000,000,000, or more captured nucleic acids per $mm^2$.

Some embodiments include a sequencing library prepared by any one of the foregoing methods.

Some embodiments of the methods and compositions provided herein include a method of preparing a sequencing library having barcodes from a double-stranded target nucleic acid comprising: (a) providing a plurality of transposomes, each transposome comprising a transposase and a transposon nucleic acid comprising a barcode; and (b) inserting the transposon nucleic acids into strands of the target nucleic acid, comprising: (i) contacting the target nucleic acid with the transposomes such that the target nucleic acid is nicked at a plurality of sites and single transposon nucleic acids are attached to the nicked strands at one side of the nicked sites, and (ii) ligating the attached single transposon nucleic acids to the nicked strands at the other side of the nicked sites, thereby obtaining a modified nucleic acid.

Some embodiments also include (c) capturing the modified target nucleic acid on a surface.

Some embodiments include a method of preparing a sequencing library having barcodes from a double-stranded target nucleic acid comprising: (a) providing a plurality of transposomes, each transposome comprising a transposase and a transposon nucleic acid comprising a barcode; and (b) inserting the transposon nucleic acids into strands of the target nucleic acid, comprising: (i) contacting the target nucleic acid with the transposomes such that the target nucleic acid is nicked at a plurality of sites and single transposon nucleic acids are attached to the nicked strands at one side of the nicked sites, and (ii) ligating the attached single transposon nucleic acids to the nicked strands at the other side of the nicked sites, thereby obtaining a modified nucleic acid; (c) amplifying the modified nucleic acid, thereby obtaining a plurality of nucleic acids comprising inserted barcodes.

Some embodiments also include capturing the modified target nucleic acid on a surface.

In some embodiments, the transposomes that are contacted with the target nucleic acids in (b) are attached to a surface, thereby capturing the modified nucleic acids on the surface.

Some embodiments also include sequencing the captured nucleic acids.

In some embodiments, the proximity of sequence information obtained from two captured nucleic acids in a linear representation of the target nucleic acid sequence is indicative of the proximity of the captured nucleic acids on the surface.

In some embodiments, captured nucleic acids in closer proximity to one another on the surface comprise sequences in closer proximity in the representation of the target nucleic acid sequence compared to captured nucleic acids in less close proximity.

In some embodiments, the representation of the target nucleic acid sequence comprises a haplotype representation.

In some embodiments, the barcode of at least one transposon nucleic acid is different.

In some embodiments, the barcodes of the transposon nucleic acids are not the same.

Some embodiments also include aligning the nucleic acid sequences according to the presence of common barcodes in the sequences to generate a representation of the target nucleic acid.

In some embodiments, the transposase comprises a one-sided transposase activity.

In some embodiments, the transposase comprises a monomer subunit lacking transposase activity.

In some embodiments, the transposase comprises covalently linked monomer subunits. In some embodiments, the quaternary structure of the transposase is monomeric. In some embodiments, the transposase lacks the ability to form dimers.

In some embodiments, the transposase is selected from the group consisting of Mu, Mu E392Q, Tn5, hyperactive Tn5, EZ-Tn5™, variants of Tn5, RAG, Tn7, Tn10, Tn552, and Vibhar transposase.

In some embodiments, the transposon nucleic acid is blocked.

In some embodiments, the 3' end of the blocked transposon nucleic acid is selected from the group consisting of a dideoxy group, a spacer group, an amine group, an azido group, alkyl group, aryl group, reverse nucleotide, a thiophosphate group, and a biotin group.

In some embodiments, the plurality of transposomes is prepared by contacting the transposases with non-functional transposon nucleic acids and functional transposon nucleic acids. In some embodiments, the non-functional transposons comprise blocked 3'-end. In some embodiments, the plurality of transposomes is prepared by contacting the transposases with blocked transposon nucleic acids and non-blocked transposon nucleic acids. In some embodiments, the ratio of transposon nucleic acids comprising blocked transposon nucleic acids to non-blocked transposon nucleic acids is greater than or equal to 1:1. In some embodiments, the ratio of transposon nucleic acids comprising blocked transposon nucleic acids to non-blocked transposon nucleic acids can be 1:2, 1:3, 1:5, 1:10, 1:20, 1:30, 1:40, 1:50, 1:75, 1:100, 2:1, 3:1, 4:1, 5:1, 6:1, 7:1, 8:1, 9:1, 10:1, 20:1, 30:1, 40:1, 50:1, 60:1, 70:1, 80:1, 90:1, or 100:1.

Some embodiments also include attaching amplification adaptors to the target nucleic acid. In some embodiments, the amplification adaptors comprise a sequence selected from the group consisting of an anchor site, a sequencing primer site, an amplification primer site, and a reporter tag.

Some embodiments also include amplifying the captured nucleic acids. In some embodiments, the amplifying of the captured nucleic acids comprises bridge amplification.

In some embodiments, the surface comprises a plurality of capture probes. In some embodiments, the capture probes comprise nucleic acids. In some embodiments, the capture probes each comprise an affinity moiety. In some embodiments, the affinity moiety is selected from the group consisting of biotin, avidin, streptavidin, and a recombinase.

In some embodiments, the transposon nucleic acid comprises a sequence selected from the group consisting of an anchor site, a sequencing primer site, an amplification primer site, a unique molecular index, and a reporter tag.

In some embodiments, at least one transposome comprises two transposon nucleic acids. In some embodiments, the two transposon nucleic acids have different sequences In some embodiments, the plurality of transposomes comprises at least two different transposon nucleic acids.

In some embodiments, the target nucleic acid is selected from the group consisting of DNA fragments of genomic DNA, and cDNA. In some embodiments, the target nucleic acid is selected from the group consisting of genomic DNA and cDNA. In some embodiments, the target nucleic acid is genomic DNA.

In some embodiments, the surface is on a substrate selected from the group consisting of a bead, slide, flow cell, channel, dip-stick, and well.

In some embodiments, the surface comprises at least about 10,000 captured nucleic acids per $mm^2$. In some embodiments, the surface comprises at least about 100,000 captured nucleic acids per $mm^2$. In some embodiments, the surface comprises at least about 1,000,000 captured nucleic acids per $mm^2$. In some embodiments, the surface comprises at least about 1,000,000, 1,500,000, 2,000,000, 3,000,000, 5,000,000, 10,000,000, 15,000,000, 20,000,000, 30,000,000, 40,000,000, 50,000,000, 60,000,000, 70,000,000, 80,000,000, 90,000,000, 100,000,000, 150,000,000, 200,000,000, 300,000,000, 350,000,000, 400,000,000, 450,000,000, 500,000,000, 550,000,000, 600,000,000, 650,000,000, 700,000,000, 750,000,000, 800,000,000, 850,000,000, 900,000,000, 950,000,000, 1000,000,000, 1200,000,000, 1300,000,000, 1400,000,000, 1500,000,000, 1600,000,000, 1700,000,000, 1800,000,000, 1900,000,000, 2000,000,000, 3000,000,000, 4000,000,000, 5000,000,000, 6000,000,000, 7000,000,000, 8000,000,000, 9000,000,000, 10, 000,000,000, or more captured nucleic acids per $mm^2$.

Some embodiments include a sequencing library comprising barcodes prepared by any one of the foregoing methods.

In some embodiments, after treatment with transposase or after a subsequent amplification, one or more recognition sequences may be added to or inserted into the nicked target nucleic acid. The one or more recognition sequences may include, but are not limited to, a barcode, a primer or an adaptor DNA sequence at the site of nicking that tags the target nucleic acid fragment as unique with respect to the adjacent, compartmental or distance spatial relationship.

After being tagged, the shotgun nucleic acid molecules may be sequenced using a sequencing platform described above contiguity information is captured by identifying recognition sequences that have a shared property. In some embodiments, the shared property is an identical or complementary barcode sequence. For example, read sequences of adjacent origin may be identified via shared barcode sequences; or reads may be defined by compartments based on shared compartment-specific barcodes derived from the same target DNA segment. In other embodiments, the shared property is a shared or constrained physical location, which may be indicated by one or more x,y coordinates on a flowcell. A "constrained" physical location may refer to a close, identical, or nearly identical physical location or to a set of two or more physical locations whose relative physical coordinates are correlated with the relative sequence coordinates on the target nucleic acid sequence from which the nucleic acid fragments were derived. For example, in methods relating to long-range contiguity, in situ transposition into stretched, HMW genomic DNA on the surface of a sequencing flowcell is performed using adaptor sequences to obtain distance spatial relationships by identification of the constrained physical locations (i.e. the relative coordinates at which physically linked sequencing templates are immobilized) of the adaptor sequences, hybridized DNA fragments, or a combination thereof. The methods can be used for capturing short-range, mid-range and long-range contiguity information.

In some embodiments, one sided transposition can be combined with combinatorial barcoding. A use of the single-sided transposed elements is one which would enable combinatorial barcoding, without the need of any additional mechanisms to hold the related library elements together during the process. An exemplary scheme of combining one-sided transposition with combinatorial barcoding is shown in FIG. 15.

DETAILED DESCRIPTION

Figure 1:
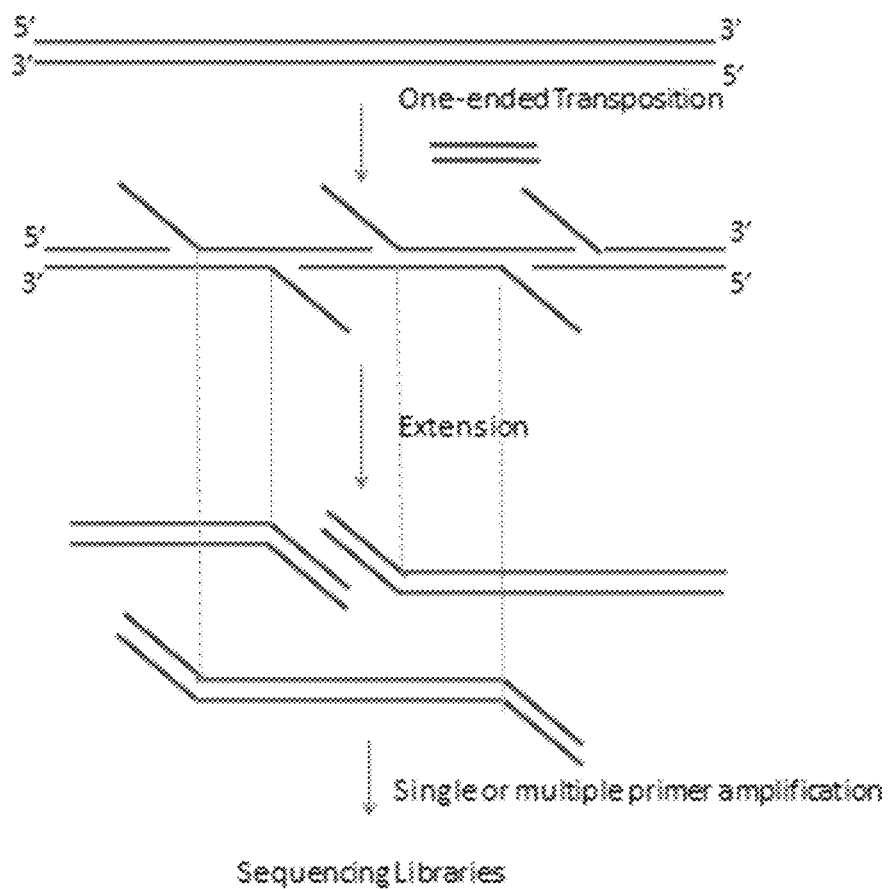
FIG. 1 depicts an example embodiment in which a target nucleic acid is contacted with a population of transposomes comprising a transposon nucleic acid.

Embodiments provided herein relate to methods and compositions for next generation sequencing. Some embodiments include the preparation of a template library from a target nucleic acid using one-sided transposition, and sequencing the template library. In some embodiments, one-sided transposition includes a transposase nicking a strand of a double-stranded nucleic acid, and attaching a transposon nucleic acid to the nicked strand at one side of the nick site. Advantageously, one-sided transposition does not fragment a double-stranded target nucleic acid as compared to a double sided transposition (e.g., Nextera™). Therefore, contiguity, haplotype, and/or phasing information can be retained for certain target nucleic acids, such as genomic DNA.

Some embodiments of the methods and compositions provided herein include transposomes having one-sided transposase activity, use of such transposomes to prepare a sequencing library, and sequencing such libraries. In some embodiments, a transposome can include a transposase having one-sided transposase activity. In some embodiments, a transposome can include a transposon nucleic acid which may have a blocking group that inhibits insertion of the transposon into both strands of a double-stranded target nucleic acid. Transposases also include integrases from retrotransposons and retroviruses transposases. Exemplary transposases include, but are not limited to Mu, Tn10, Tn5, and hyperactive Tn5 (Goryshin and Reznikoff, J. Biol. Chem., 273:7367 (1998)). Embodiments of transposases useful with some of the methods and compositions provided herein include those disclosed in U.S. Pat. App. Pub. No. 2010/0120098, which is incorporated herein by reference in its entirety. More embodiments of transposases and transposon elements include a hyperactive Tn5 transposase and a Tn5-type transposase element (Goryshin and Reznikoff, J. Biol. Chem., 273:7367 (1998), which is incorporated herein by reference in its entirety), MuA transposase and a Mu transposase element comprising R1 and R2 end sequences (Mizuuchi, Cell, 35: 785, (1983) and Savilahti, et al., EMBO J., 14: 4893, 15 (1995), each of which is incorporated herein by reference in its entirety). Example transposase elements that form a complex with a hyperactive Tn5 transposase (e.g., EZ-Tn5™ Transposase, Epicentre Biotechnologies, Madison, Wisconsin) are set forth in WO 2012/061832; U.S. 2012/0208724, U.S. 2012/0208705 and WO 2014018423, each of which is incorporated herein by reference in its entirety. More embodiments of transposases and transposon sequences useful with some of the methods and compositions provided herein include *Staphylococcus aureus* Tn552 (Colegio et al., J. Bacteriol., 183: 2384-8 (2001); Kirby et al., Mol. Microbiol., 43: 173-86 (2002)), Ty1 (Devine & Boeke, Nucleic Acids Res., 22: 3765-72 (1994) and WO 95/23875), Transposon Tn7 (Craig, Science 271: 1512 (1996); Craig, Curr Top Microbiol Immunol., 204:27-48 (1996)), Tn/O and IS10 (Kleckner et al., Curr Top Microbiol Immunol., 204:49-82 (1996)), Mariner transposase (Lampe et al., EMBO J., 15: 5470-9, (1996)), Tel (Plasterk, Curro Topics Microbiol. Immunol., 204: 125-43, (1996)), P Element (Gloor, Methods Mol. Biol., 260: 97-114, (2004)), Tn3 (Ichikawa & Ohtsubo, J Biol. Chem. 265: 18829-32, (1990)), bacterial insertion sequences (Ohtsubo & Sekine, Curro Top. Microbiol. Immunol. 204: 1-26, (1996)), retroviruses (Brown, et al., Proc Natl Acad Sci USA, 86:2525-9, (1989)), and retrotransposon of yeast (Boeke & Corces, Annu Rev Microbiol. 43:403-34, (1989)). More examples include IS5, Tn10, Tn903, IS911, and engineered versions of transposase family enzymes (Zhang et al., PLOS Genet. 5:el000689. Epub 2009 Oct. 16; and Wilson et al. Microbiol. Methods 71:332-5 (2007)). More examples include MuA transposases (See e.g., Rasila T S, et al., (2012) PLOS ONE 7(5): c37922. doi:10.1371/journal.pone.0037922). Examples of transposases useful with some embodiments of the methods and compositions provided herein are described in Leschziner, A. E., et al., (1998) P.N.A.S. 95:7345-7350; and Haapa S., et al., (1999) N. A. Res. 27:2777-2784, which are each incorporated by reference in its entirety. Variants of Tn5 transposases, such as having amino acid substitutions, insertions, deletions, and/or fusions with other proteins or peptides are disclosed in U.S. Pat. Nos. 5,925,545; 5,965, 443; 7,083,980; 7,608,434; and U.S. patent application Ser. No. 14/686,961. The patents and the patent application are incorporated herein by reference in its entirety. In some embodiments, the Tn5 transposase comprise one or more substitutions at positions 54, 56, 372, 212, 214, 251, and 338 with respect to the wild type protein as disclosed in U.S. patent application Ser. No. 14/686,961. In some embodiments, the Tn5 wild-type protein or its variant can further comprise a fusion polypeptide. In some embodiments, the polypeptide domain fused to the transposase can comprise, for example, Elongation Factor Ts. Each of the references cited in this paragraph is incorporated herein by reference in its entirety.

In some embodiments, a double-stranded target nucleic acid is contacted with a plurality of transposomes such that strands of target nucleic acid are nicked and transposon nucleic acids are attached to strands of the nicked target nucleic acid at one side of the nick sites to obtain a modified target nucleic acid. In some embodiments, the transposome contacts the target nucleic acid in solution. In this embodiment, the modified target nucleic acid can be produced in solution and subsequently captured on a surface. Alternatively, contact between the transposome and target nucleic acid can occur on a surface. The transposome or the target nucleic acid can be attached to the surface prior to the contact being made. The modified target nucleic acid that results from contact between the transposome and target nucleic acid on the surface can remain captured on the surface or the modified target nucleic acid can be released from the surface.

In some embodiments, the captured nucleic acid is sequenced. In some embodiments, the proximity of sequence information obtained from two captured nucleic acids in a linear representation of the target nucleic acid sequence is indicative of the proximity of the captured nucleic acids on the surface. In some embodiments, captured nucleic acids in closer proximity to one another on the surface comprise sequences in closer proximity in the representation of the target nucleic acid sequence compared to captured nucleic acids in less close proximity. In some embodiments, the representation of the target nucleic acid sequence comprises a haplotype or assembly representation.

Some embodiments of the methods and compositions provided herein also include the use of one-sided transposition in de novo assembly of sequenced fragments of a target nucleic acid. In some embodiments, landmarks are inserted into a target nucleic acid and can be used in the assembly of sequenced fragments of a target nucleic to generate a representation of the target nucleic acid sequence. In some embodiments, overlapping fragments can include common inserted landmarks. The use of landmarks is particularly advantageous with target nucleic acids comprising highly repetitive sequences. Also, in some embodiments, no reference sequence is required.

In some embodiments, landmarks are inserted into a target nucleic acid by contacting the target nucleic acid with a population of transposomes having one-sided transposase activity, and transposon nucleic acids comprising different barcodes. In some embodiments, the transposon nucleic acids are inserted into single-strands of the target nucleic acid by one-side transposition and then ligation. In some embodiments, the transposase nicks a strand of target nucleic acid, and the transposon nucleic acid is attached to one strand of the nicked target nucleic acid at the nicked site, and the other end of the transposon nucleic acid is ligated to the nicked target nucleic acid at the other side of the nicked side, thereby obtaining a modified double-stranded target nucleic acid having an insertion in on strand comprising a loop. In some embodiments the modified nucleic acid can be amplified and sequenced. In some embodiments, the modified nucleic acid can be attached to a surface. In some embodiments, attachment can be made through a single-strand binding protein, or protein that binds single strand loops, such as a recombinase.

Figure 12:
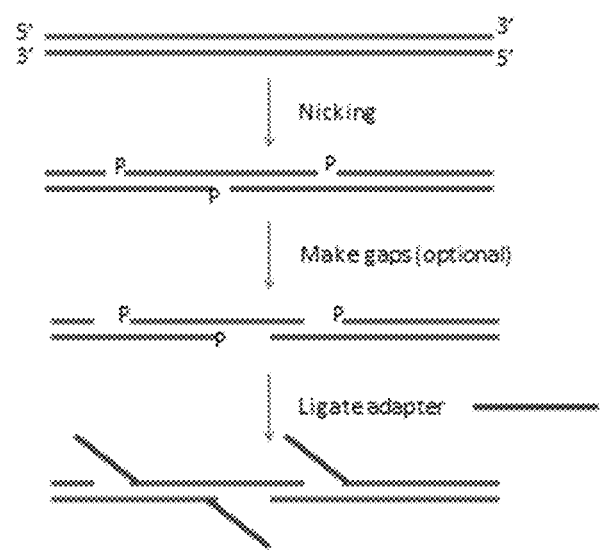
FIG. 12 shows an exemplary scheme of nicking the target nucleic acid and ligating the oligonucleotide adapter.
Figure 13:
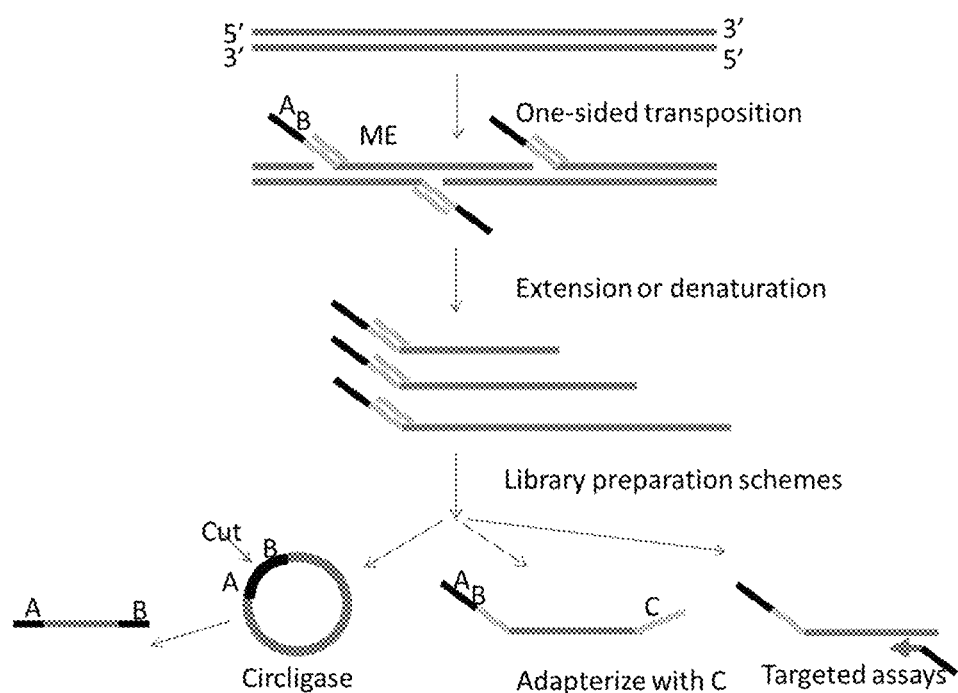
FIG. 13 shows exemplary schemes of library preparation using one sided transposition.
Figure 14:
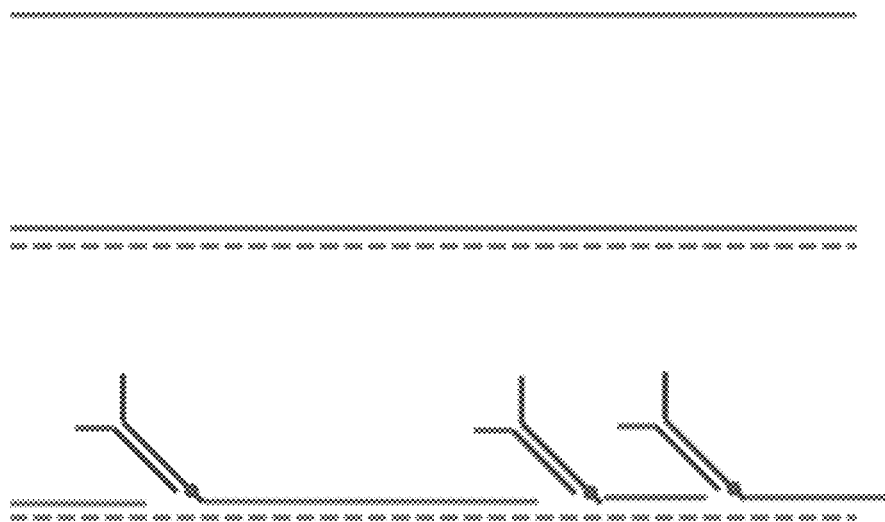
FIG. 14 shows an exemplary scheme of one-sided transposition by exploiting the differential resistance to transposition by two strands of a DNA.
Figure 15:
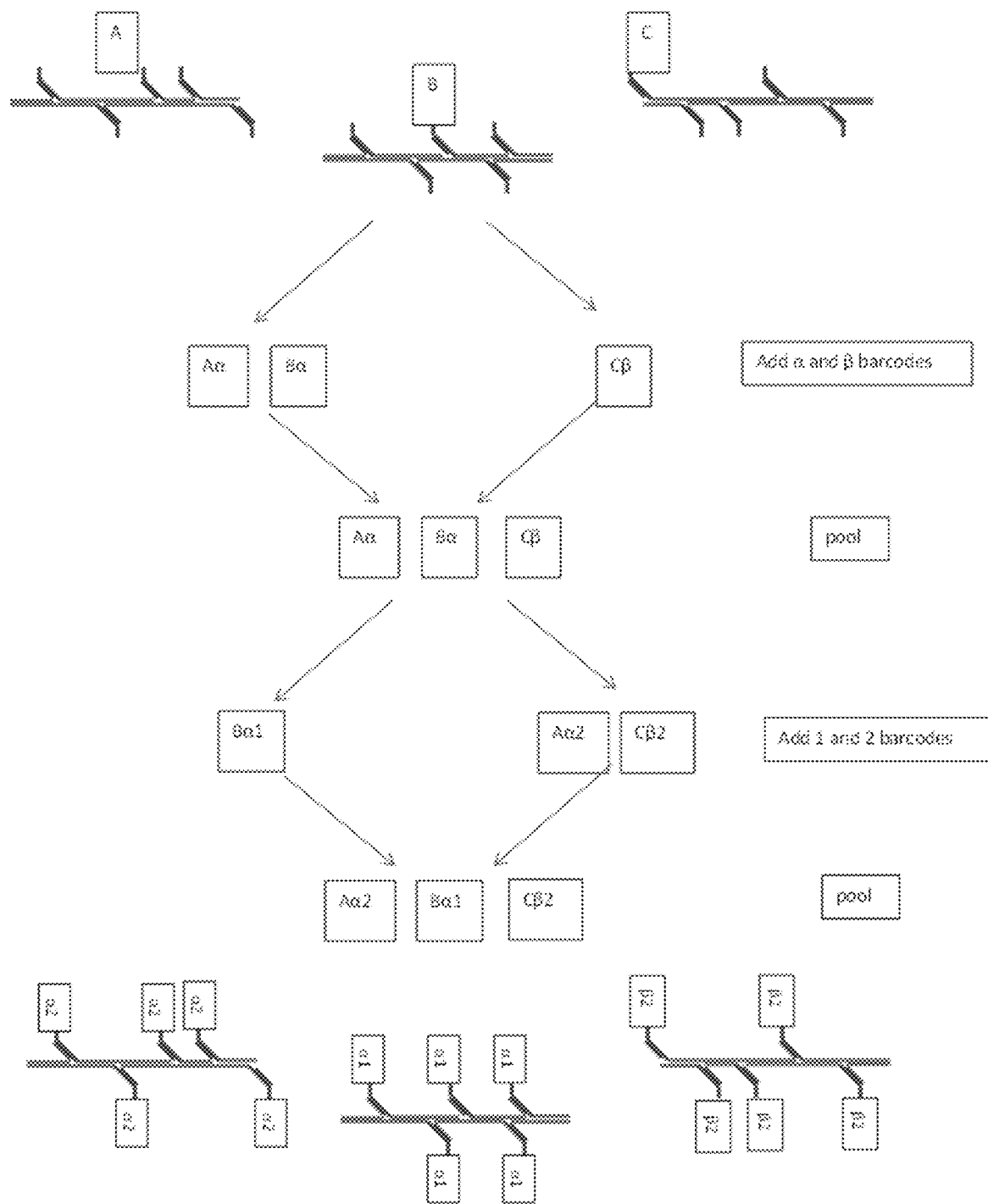
FIG. 15 shows an exemplary scheme of one-sided transposition coupled with combinatorial bar coding. Using the one-sided transposition the single-sided products themselves can maintain contiguity without the need of an external mechanism. Unique, but indistinguishable molecules, (A, B, and C) are contained together. They are randomly split into separate reactions, in which modular barcodes are added. Although the number of separated reactions at each step is fewer than the number of molecules, the path through the reactions tends to be unique for each molecule, resulting in a unique barcode combination for each.

In some embodiments, target nucleic acid is modified without transposition. In some embodiments, target nucleic acid can be randomly using nicking endonuclease, e.g., nicking endonuclease from New England Biolabs, MA, USA, or restriction endonucleases. Exemplary restriction endonucleases include but are not limited to EcoRI, EcoRII, BamHI, Hind III, TaqI, NotI. Other examples of restriction endonucleases can be found in New England Biolabs catalog. Optionally, gaps can be extended with enzymes having 3' or 5' exonuclease activity, for example with Exonuclease I or Exonuclease II, or Exonuclease III. Oligonucleotide adapters can be ligated to the nicked end of the target nucleic acid. In some embodiments, oligonucleotide adapters can include a primer binding site, such as a sequencing primer site, and an amplification primer site, additional sequences can also include a cleavage site, a unique molecular index, an anchor site, a reporter tag, and a barcode. Thus, nicking the target nucleic acid and ligating one or more adapters keeps the target nucleic acid intact without fragmentation. Exemplary scheme of nicking the target nucleic acid and ligating the oligonucleotide adapter is shown in FIG. 12.

As used herein, "nucleic acid" includes at least two nucleotide monomers linked together. Examples include, but are not limited to DNA, such as genomic or cDNA; RNA, such as mRNA, sRNA or rRNA; or a hybrid of DNA and RNA. As apparent from the examples below and elsewhere herein, a nucleic acid can have a naturally occurring nucleic acid structure or a non-naturally occurring nucleic acid analog structure. A nucleic acid can contain phosphodiester bonds; however, in some embodiments, nucleic acids may have other types of backbones, comprising, for example, phosphoramide, phosphorothioate, phosphorodithioate, O-methylphosphoroamidite and peptide nucleic acid backbones and linkages. Nucleic acids can have positive backbones; non-ionic backbones, and non-ribose based backbones. Nucleic acids may also contain one or more carbocyclic sugars. The nucleic acids used in methods or compositions herein may be single stranded or, alternatively double stranded, as specified. In some embodiments a nucleic acid can contain portions of both double stranded and single stranded sequence, for example, as demonstrated by forked adapters. A nucleic acid can contain any combination of deoxyribo- and ribonucleotides, and any combination of bases, including uracil, adenine, thymine, cytosine, guanine, inosine, xanthine, hypoxanthanine, isocytosine, isoguanine, and base analogs such as nitropyrrole (including 3-nitropyrrole) and nitroindole (including 5-nitroindole), etc. In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole. Promiscuous bases that can base-pair with at least two, three, four or more types of bases can be used.

As used herein, "nucleotide sequence" includes the order and type of nucleotide monomers in a nucleic acid polymer. A nucleotide sequence is a characteristic of a nucleic acid molecule and can be represented in any of a variety of formats including, for example, a depiction, image, electronic medium, series of symbols, series of numbers, series of letters, series of colors, etc. The information can be represented, for example, at single nucleotide resolution, at higher resolution (e.g. indicating molecular structure for nucleotide subunits) or at lower resolution (e.g. indicating chromosomal regions, such as haplotype blocks). A series of "A," "T," "G," and "C" letters is a well-known sequence representation for DNA that can be correlated, at single nucleotide resolution, with the actual sequence of a DNA molecule. A similar representation is used for RNA except that "T" is replaced with "U" in the series.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. Universal sequences can occur at the ends of a nucleic acid, or flanking a region of nucleic acid that is to be copied, detected or amplified.

As used herein, "haplotype" includes a set of alleles at more than one locus inherited by an individual from one of its parents. A haplotype can include two or more loci from all or part of a chromosome. Alleles include, for example, single nucleotide polymorphisms (SNPs), short tandem repeats (STRs), gene sequences, chromosomal insertions, chromosomal deletions etc. The term "phased alleles" refers to the distribution of the particular alleles from a particular chromosome, or portion thereof. Accordingly, the "phase" of two alleles can refer to a characterization or representation of the relative location of two or more alleles on one or more chromosomes.

As used herein, a "nick" in a nucleic acid means a region of a double stranded nucleic acid where only one of the two strands contains a cleaved backbone structure. Thus, "nicking" refers to the act of breaking the covalent structure of only one nucleic acid strand within a region of a double stranded nucleic acid. The region is generally only a portion of the double stranded nucleic acid. The portion can include, for example, at most 5 base pairs, 10 base pairs, 25 base pairs, 50 base pairs, 100 base pairs, 200 base pairs, 300 base pairs, 400 base pairs, 500 base pairs, 1000 base pairs. The regions can include larger portions or smaller portions of a double stranded nucleic acid. For example, alternatively or additionally to the upper limits exemplified above, the lower limit of a portion of a nucleic acid that is nicked can optionally be at least 500 base pairs, 400 base pairs, 300 base pairs, 200 base pairs, 100 base pairs, 50 base pairs, 25 base pairs, 10 base pairs or smaller. The values listed in the above ranges can define the maximum or minimum size for all members of a population of nucleic acid regions or alternatively can refer to an average for the population of nucleic acids having the regions. It will be understood that a double stranded nucleic acid can be nicked in both strands, a first nick occurring in a first region and a second nick occurring in a second region. Generally, the effective connectivity of the two nicked regions can be maintained under conditions where the nucleic acid remains in a hybridized, double stranded form. In contrast, cleaving both strands in the same region of a double stranded nucleic acid can result in loss of effective connectivity between regions of the nucleic acid that flank the site of cleavage.

As used herein, the term "surface" is intended to mean part or layer of a solid support or gel material that is in direct contact with a surrounding fluid such as a gaseous fluid or liquid fluid. The surface can be in contact with another material such as a gas, liquid, gel, polymer, organic polymer, second surface of a similar or different material, metal, or coat. The surface, or regions thereof, can be substantially flat. The surface can have surface features such as wells, pits, channels, ridges, raised regions, pegs, posts or the like. In the case of a porous substrate a surface can be located in a pore where a fluid is in contact with the substrate. For example, a surface can occur in the pores of a gel where attached moieties interact with fluid that enters the pores. Thus, a moiety that is "on" a surface may be located in a pore of a porous material such as a gel.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are located within a flow cell apparatus.

As used herein, the term "gel material" is intended to mean a semi-rigid substrate that is permeable to liquids and gases. Typically, gel material can swell when liquid is taken up and can contract when liquid is removed by drying. Exemplary gels include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, U.S. Prov. Pat. App. Ser. No. 61/753,833, which is incorporated herein by reference).

As used herein, the term "attached" is intended to mean connected by forces that prevent separation by diffusion. The term can include connections that are covalent or non-covalent in nature. For example a nucleic acid can be covalently attached to a surface through one or more covalent bonds that create a chain of bonds. Non-covalent attachment occurs when at least one of the bonds between two things (e.g. between a nucleic acid and a surface) is not a covalent bond. Examples of non-covalent bonds include, for example, hydrogen bonds, ionic bonds, van der Waals forces, hydrophobic bonds or the like.

As used herein, the term "contiguity information" refers to a spatial relationship between two or more DNA fragments based on shared information. The shared aspect of the information can be with respect to adjacent, compartmental and distance spatial relationships. Information regarding these relationships in turn facilitates hierarchical assembly or mapping of sequence reads derived from the DNA fragments. This contiguity information improves the efficiency and accuracy of such assembly or mapping because traditional assembly or mapping methods used in association with conventional shotgun sequencing do not take into account the relative genomic origins or coordinates of the individual sequence reads as they relate to the spatial relationship between the two or more DNA fragments from which the individual sequence reads were derived. Therefore, according to the embodiments described herein, methods of capturing contiguity information may be accomplished by short range contiguity methods to determine adjacent spatial relationships, mid-range contiguity methods to determine compartmental spatial relationships, or long range contiguity methods to determine distance spatial relationships. These methods facilitate the accuracy and quality of DNA sequence assembly or mapping, and may be used with any sequencing method, such as those described above.

In some embodiments, this step results in the generation of a library of shotgun nucleic acid molecules derived from the target DNA sequence. In an alternative embodiment, the fragmentation or insertion even may be accomplished by a Y adaptor approach as described below. The one or more transposase molecules may be soluble free transposase or may be associated with a surface-bound recognition sequence.

As used herein the term "barcode" refers to a nucleic acid sequence that is unique to and entirely independent of the target nucleic acid sequence. Generally, a barcode can include one or more nucleotide sequences that can be used to identify one or more particular nucleic acids. The barcode can be an artificial sequence, or can be a naturally occurring sequence generated during transposition, such as identical flanking genomic DNA sequences (g-codes) at the end of formerly juxtaposed DNA fragments. A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated.

In some embodiments, a transposon sequence comprises at least one barcode. In some embodiments, such as transposomes comprising two non-contiguous transposon sequences, the first transposon sequence comprises a first barcode, and the second transposon sequence comprises a second barcode. In some embodiments, a transposon sequence comprises a barcode comprising a first barcode sequence and a second barcode sequence. In some of the foregoing embodiments, the first barcode sequence can be identified or designated to be paired with the second barcode sequence. For example, a known first barcode sequence can be known to be paired with a known second barcode sequence using a reference table comprising a plurality of first and second bar code sequences known to be paired to one another.

In another example, the first barcode sequence can comprise the same sequence as the second barcode sequence. In another example, the first barcode sequence can comprise the reverse complement of the second barcode sequence. In some embodiments, the first barcode sequence and the second barcode sequence are different. The first and second barcode sequences may comprise a bi-code.

In some embodiments of compositions and methods described herein, barcodes are used in the preparation of template nucleic acids. As will be understood, the vast number of available barcodes permits each template nucleic acid molecule to comprise a unique identification. Unique identification of each molecule in a mixture of template nucleic acids can be used in several applications. For example, uniquely identified molecules can be applied to identify individual nucleic acid molecules, in samples having multiple chromosomes, in genomes, in cells, in cell types, in cell disease states, and in species, for example, in haplotype sequencing, in parental allele discrimination, in metagenomic sequencing, and in sample sequencing of a genome.

In some embodiments, a plurality of unique barcodes throughout the target nucleic acid may be inserted during transposition. In some embodiments, each barcode includes a first barcode sequence and a second barcode sequence, having a fragmentation site disposed therebetween. The first barcode sequence and second barcode sequence can be identified or designated to be paired with one another. The pairing can be informative so that a first barcode is associated with a second barcode. Advantageously, the paired barcode sequences can be used to assemble sequencing data from the library of template nucleic acids. For example, identifying a first template nucleic acid comprising a first barcode sequence and a second template nucleic acid comprising a second barcode sequence that is paired with the first indicates that the first and second template nucleic acids represent sequences adjacent to one another in a sequence representation of the target nucleic acid. Such methods can be used to assemble a sequence representation of a target nucleic acid de novo, without the requirement of a reference genome.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

As used herein, the term "about" means+/−10%.

Target Nucleic Acids

Some embodiments of the methods and compositions provided herein include a target nucleic acid. In some embodiments, a target nucleic acid includes a double-stranded nucleic acid. In some embodiments, a target nucleic acid includes genomic DNA, or cDNA. In some embodiments, mitochondrial or chloroplast DNA is used. In some embodiments, target nucleic acids include RNA or derivatives thereof such as mRNA or cDNA. Some embodiments described herein can utilize a single target nucleic acid species, present in one copy (i.e. single molecule) or, alternatively present in multiple copies (i.e. an ensemble of nucleic acid molecules having the same sequence). Other embodiments can utilize a plurality of different target nucleic acid species (e.g., nucleic acid molecules having different nucleotide sequences being present in the plurality). Thus, a plurality of target nucleic acids can include a plurality of the same target nucleic acids, a plurality of different target nucleic acids where some target nucleic acids are the same, or a plurality of target nucleic acids where all target nucleic acids are different. Target nucleic acids may be prepared from nucleic acid molecules obtained from a single organism or from populations of nucleic acid molecules obtained from sources that include more than one organism. A target nucleic acid can be from a single cell; from multiple cells, tissue(s) or bodily fluids of a single organism; from cells, tissues or bodily fluids of several organisms of the same species; or from multiple species, as with metagenomic samples, such as from environmental samples. Sources of nucleic acid molecules include, but are not limited to, organelles, cells, tissues, organs, or organisms.

In some embodiments, a target nucleic acid is contacted with a transposome such that the transposon nucleic acid inserts into or attaches to the target nucleic acid to provide a modified nucleic acid. In some embodiments, modified nucleic acids may be further manipulated, for example extended, amplified, and ligated.

Transposomes

Some embodiments of the methods and compositions provided herein include transposomes. In some embodiments, a transposome includes a transposase bound to one or more transposon nucleic acids. In some embodiments, the transposome comprises a one-sided transposase activity which includes nicking a strand of a double-stranded nucleic acid, and attaching a transposon nucleic acid to the nicked strand at one side of the nick site.

In some embodiments, transposomes having one-sided transposase activity include transposomes comprising certain types of transposases having one-sided transposase activity. In some embodiments, a wild type transposase has one-sided transposase activity or is modified to have one-sided transposase activity. Examples of transposases with one-sided transposase activity or that may be modified to have one-sided transposase activity include Mu, Mu E392Q, Tn5, RAG, hyperactive Tn5, Tn5 variants, Vibhar, and Tn552 (Leschziner, A. E., et al., (1998) P.N.A.S. 95:7345-7350; and Haapa S., et al., (1999) N. A. Res. 27:2777-2784, which are each incorporated by reference in its entirety). More examples of transposases with one-sided transposase activity or that may be modified to have one-sided transposase activity are listed herein. In some embodiments, a transposome having one-sided transposase activity comprises a single monomer and a transposon nucleic acid. In some embodiments a transposase may be modified to lack the ability to form a dimer. In some embodiments, a transposome having one-sided transposase activity comprises a dimer in which one of the monomers lacks transposase activity. In some embodiments, the monomer subunits of the dimer may be covalently linked.

In some embodiments, a transposome having one-sided transposase activity comprises a blocked transposon nucleic acid. In some embodiments, a blocked transposon nucleic acid is blocked from being attached to a strand of a nicked double-stranded nucleic acid. The blocked transposon nucleic acid can include blocking groups at the 3' end of the transposon nucleic acid that inhibit attachment of the transposon nucleic acid to another nucleic acid. In some embodiments, blocking groups can include a dideoxy group, a spacer group, and a biotin group. In some embodiments, a population of transposomes having one-sided transposase activity can be prepared by contacting transposases with blocked transposon nucleic acids and non-blocked transposon nucleic acids. Non-blocked transposon nucleic acids include transposon nucleic acids that lack blocking groups. In some embodiments, a population is obtained that includes transposomes comprising transposase dimers comprising a blocked transposon nucleic acid and a non-blocked transposon nucleic acid. In some embodiments, transposase dimers comprise two blocked transposon nucleic acids. In some embodiments, transposase dimers comprise two non-blocked transposon nucleic acids. In some embodiments, the proportion of the different types of dimers in a population can be manipulated by contacting the transposases with various ratios of blocked transposon nucleic acids to non-blocked transposon nucleic acids. In some embodiments, the ratio of blocked transposon nucleic acids to non-blocked transposon nucleic acids is greater than or equal to 1:1, 5:1, 10:1, 50:1, 100:1, 200:1, 500:1, 1000:1, or any range between the foregoing ratios.

Other useful transposon nucleic acids are those that are shorter or longer than standard transposon. For example, the transferred strand at the 3' end can be made shorter (e.g. by removing one or more bases) to inhibit the transfer reaction from occurring. Similarly, the 3' end can be longer to result in such inhibition.

Methods for single-sided transposition can also be used for regulating the insert size of the library after transposition. An advantage of such an approach is that the length of the insert size can be determined by the ratio between active and non-active complex, which in many situations is easier to control than time of incubation or concentration of transposome and nucleic acid.

Figure 11:
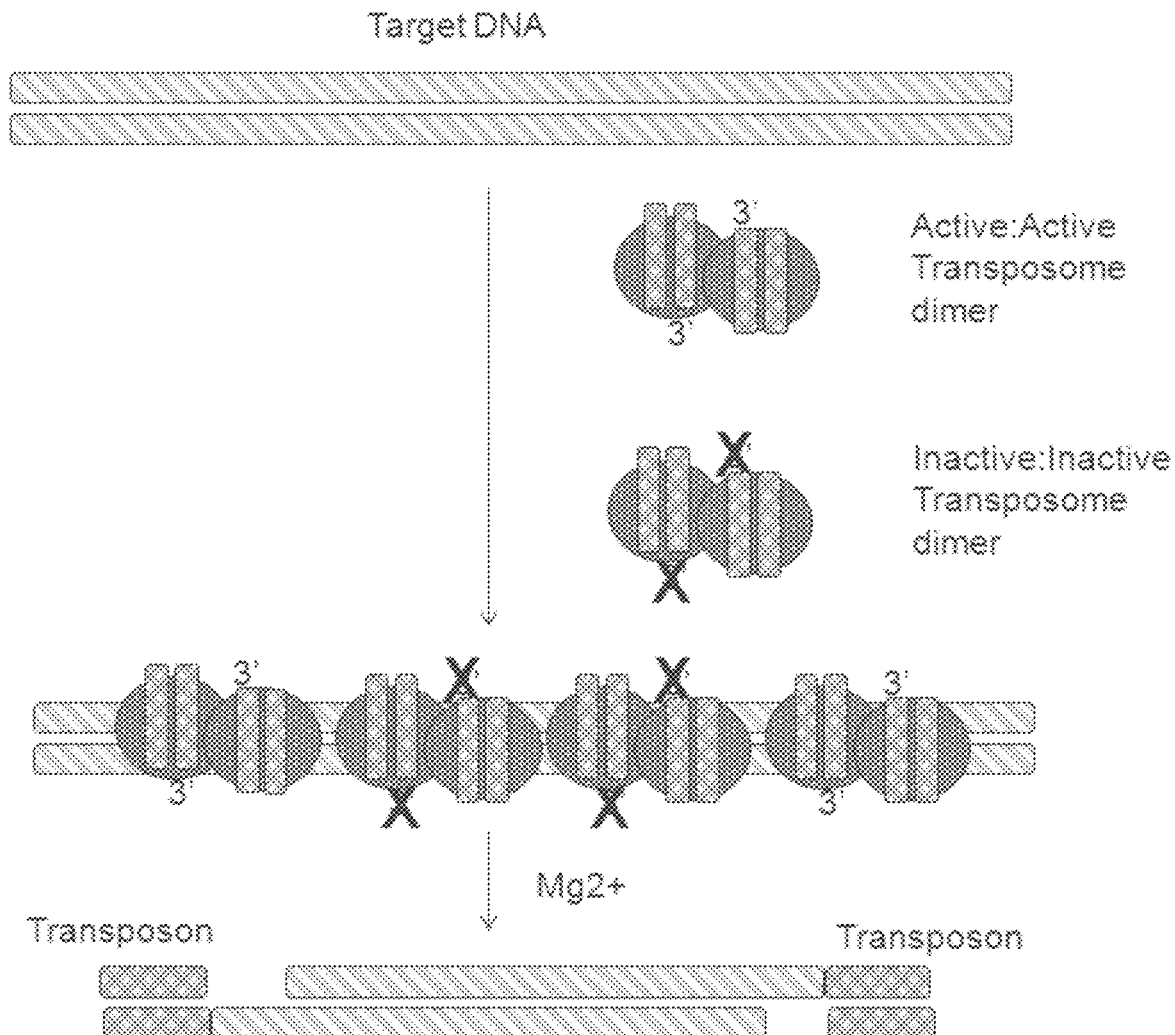
FIG. 11 shows a diagram of a transposition reaction carried out with a mixture of active and inactive transposomes.

Transposome dimers having an active transposome monomeric subunit and a non-active transposome subunit can be prepared and added to nucleic acids before or after a transposition reaction is started. For example, the reaction can be started by addition of $Mg^{2+}$. In particular embodiments a population that includes a mixture of three species of transposome dimers (i.e. active: active dimers, inactive: inactive dimers, and active: inactive dimers) can be formed. Populations having different activities can be prepared by altering the ratio of active and non-active transposome subunits that are combined to form a mixture. The ratio can be selected to influence the average insert size that is produced when a nucleic acid sample is treated with the mixture. Similar control of insert size can be achieved by using a mixture of transposome species having only the two transposome species of active: active and inactive:

inactive. As demonstrated by the diagram in FIG. 11, the inactive: inactive species being capable of binding to the target DNA but incapable of transposing the target, will act as spacers. In other words the inactive: inactive dimers compete for sites that would otherwise be bound to active: active dimers and transposed. Routine titration of the amount of inactive: inactive dimer that is spiked into a transposase reaction mixture can be used to control average fragment sizes produced by the mixture. These methods have several advantages including for example, being relatively time-independent and controllable. Conventional transposition reactions (e.g. Nextera® Sample Preparation methods from Illumina, Inc. (San Diego, CA)) require careful control of the reaction time period to achieve a transposition reaction that produces fragments of a desired average size. The current methods of one-sided transposition, on the other hand, can be carried out as set forth above to be less time sensitive. More specifically, the ratio of active to inactive monomer subunits can be selected to determine size of the fragments in the library.

In some embodiments, a transposome having one-sided transposase activity can be attached to a surface. The transposome can be attached via the transposase or via the transposon nucleic acid. For example, a transposase can be covalently or non-covalently attached to a surface. Alternatively or additionally, a transposon nucleic acid can be covalently or non-covalently attached to the surface. Useful attachments, surfaces and associated methods for their preparation and use are set forth in further detail herein and in U.S. patent application Ser. No. 13/790,220, which is incorporated herein by reference.

In some embodiments, a transposase includes an enzyme that is capable of forming a functional complex with a transposon nucleic acid comprising a transposon element or transposase element, and catalyzing insertion or transposition of the transposon nucleic acid into a target nucleic acid to provide a modified nucleic acid. For example, in an in vitro transposition reaction, inserting transposon nucleic acids into a target DNA to provide a modified DNA. In some embodiments, a transposase includes an enzyme that is capable of forming a functional complex with a transposon nucleic acid comprising a transposon element or transposase element, and catalyzing one-sided transposition into a target nucleic acid to provide a modified nucleic acid.

In some embodiments, insertion or attachment of transposon nucleic acids by a transposase can be at a random or substantially random site in a target nucleic acid.

Transposases also include integrases from retrotransposons and retroviruses transposases. Embodiments of transposases useful with some of the methods and compositions provided herein include those disclosed in U.S. 2010/0120098, which is incorporated herein by reference in its entirety. More embodiments of transposases and transposon elements include a hyperactive Tn5 transposase and a Tn5-type transposase element (Goryshin and Reznikoff, J. Biol. Chem., 273:7367 (1998), which is incorporated herein by reference in its entirety), MuA transposase and a Mu transposase element comprising R1 and R2 end sequences (Mizuuchi, Cell, 35: 785, (1983) and Savilahti, et al., EMBO J., 14: 4893, 15 (1995), each of which is incorporated herein by reference in its entirety). Example transposase elements that form a complex with a hyperactive Tn5 transposase (e.g., EZ-Tn5™ Transposase, Epicentre Biotechnologies, Madison, Wisconsin) are set forth in WO 2012/061832; U.S. 2012/0208724, U.S. 2012/0208705 and WO 2014018423, each of which is incorporated herein by reference in its entirety. More embodiments of transposases and transposon nucleic acids useful with some of the methods and compositions provided herein include *Staphylococcus aureus* Tn552 (Colegio et al., J. Bacteriol., 183: 2384-8 (2001); Kirby et al., Mol. Microbiol., 43: 173-86 (2002)), Ty1 (Devine & Bocke, Nucleic Acids Res., 22: 3765-72 (1994) and WO 95/23875), Transposon Tn7 (Craig, Science 271: 1512 (1996); Craig, Curr Top Microbiol Immunol., 204:27-48 (1996)), Tn/O and IS10 (Kleckner et al., Curr Top Microbiol Immunol., 204:49-82 (1996)), Mariner transposase (Lampe et al., EMBO J., 15: 5470-9, (1996)), Tel (Plasterk, Curro Topics Microbiol. Immunol., 204: 125-43, (1996)), P Element (Gloor, Methods Mol. Biol., 260: 97-114, (2004)), Mos-1 transposase (Richardson et al., EMBO Journal 25:1324-1334 (2006)), Tn3 (Ichikawa & Ohtsubo, J Biol. Chem. 265: 18829-32, (1990)), bacterial insertion sequences (Ohtsubo & Sekine, Curro Top. Microbiol. Immunol. 204: 1-26, (1996)), retroviruses (Brown, et al., Proc Natl Acad Sci USA, 86:2525-9, (1989)), and retrotransposon of yeast (Bocke & Corces, Annu Rev Microbiol. 43:403-34, (1989)). More examples include IS5, Tn10, Tn903, IS911, and engineered versions of transposase family enzymes (Zhang et al., PLOS Genet. 5:e1000689. Epub 2009 Oct. 16; and Wilson et al. Microbiol. Methods 71:332-5 (2007)). More examples include MuA transposases (See e.g., Rasila T S, et al., (2012) PLOS ONE 7(5): e37922. doi: 10.1371/journal.pone.0037922). Each of the references cited in this paragraph is incorporated herein by reference in its entirety.

In some embodiments, a transposon nucleic acid comprises a double-stranded nucleic acid. A transposon element includes a nucleic acid molecule, or portion thereof, that includes the nucleotide sequences that forms a transposome with a transposase or integrase enzyme. In some embodiments, a transposon element is capable of forming a functional complex with the transposase in a transposition reaction. Examples of transposon elements are provided herein, and include the 19-bp outer end ("OE") transposon end, inner end ("IE") transposon end, or "mosaic end" ("ME") transposon end recognized by, for example, a wild-type or mutant Tn5 transposase, or the R1 and R2 transposon end (See e.g., US 2010/0120098, which is incorporated herein by reference in its entirety). Transposon elements can comprise any nucleic acid or nucleic acid analogue suitable for forming a functional complex with the transposase or integrase enzyme in an in vitro transposition reaction. For example, the transposon end can comprise DNA, RNA, modified bases, non-natural bases, modified backbone, and can comprise nicks in one or both strands.

In some embodiments, a transposon nucleic acid can include a transposon element and additional sequences. In some embodiments, the additional sequences can be inserted into or attached to a target nucleic acid in a transposition reaction. The additional sequences can include a primer binding site, such as a sequencing primer site, and an amplification primer site, additional sequences can also include a cleavage site, an unique molecular index, an anchor site, a reporter tag, and a barcode.

In some embodiments, a primer binding site can include sequences for sequencing primers to anneal to a nucleic acid in a sequencing reaction. In some embodiments, a primer binding site can include sequences for primers to anneal to a nucleic acid in an amplification reaction or other extension reaction.

In some embodiments, a cleavage site can include a site in a transposon nucleic acid that can be fragmented. For example, a transposon nucleic acid comprising a cleavage site can be inserted into a target nucleic acid and the modified nucleic acid can then be fragmented at the inserted cleavage site. In some embodiments, a cleavage site includes a restriction enzyme recognition sequence and/or a restriction enzyme cleavage site. In some embodiments, a cleavage site can include at least one ribonucleotide in a nucleic acid that may otherwise comprise deoxyribonucleotides and may be cleaved with an RNAse. Chemical cleavage agents capable of selectively cleaving the phosphodiester bond between a deoxyribonucleotide and a ribonucleotide can be used including, for example, metal ions such as rare-earth metal ions (e.g., $La^{3+}$, particularly $Tm^{3+}$, $Yb^{3+}$ or $Lu^{3+}$, Fe(3) or Cu(3)), or exposure to elevated pH. In some embodiments, a cleavage site can include one or more recognition sequences for a nickase, that is, a nicking endonuclease that breaks one strand of a particular region of a double-stranded nucleic acid. Thus, the fragmentation site can include a first nickase recognition sequence, and optionally a second nickase recognition sequence. The first and second nickase recognition sequences can be the same as each other or different from each other. In some embodiments, a cleavage site can include one or more nucleotide analogues that comprise an abasic site and permits cleavage at the fragmentation site in the presence of certain chemical agents, such as polyamine, N,N'-dimethylethylenediamine (DMED) (See e.g., U.S. 2010/0022403, which is incorporated herein by reference in its entirety). In some embodiments, an abasic site may be created by modification of a uracil nucleotide within the cleavage site, for example, using a uracil DNA glycosylase (UDG) enzyme. The polynucleotide strand including the abasic site may then be cleaved at the abasic site by treatment with endonuclease (e.g. Endo IV endonuclease, AP lyase, FPG glycosylase/AP lyase, Endo VIII glycosylase/AP lyase), heat or alkali. Abasic sites may also be generated at nucleotide analogues other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease such as Endo IV or AP lyase (See e.g., U.S. 2011/0014657, which is incorporated herein by reference in its entirety). In another example, a cleavage site may include a diol linkage which permits cleavage by treatment with periodate (e.g., sodium periodate). In another example, a cleavage site may include a disulfide group which permits cleavage with a chemical reducing agent, e.g. Tris (2-carboxyethyl)-phosphate hydrochloride (TCEP). In some embodiments, a cleavage site may include a photocleavable moiety. Photochemical cleavage can be carried out by any of a variety of methods that utilize light energy to break covalent bonds. A site for photochemical cleavage can be provided by a non-nucleotide chemical moiety in a nucleic acid, such as phosphoramidite [4-(4,4'-dimethoxytrityloxy)butyramidomethyl)-1-(2-nitrophenyl)-ethyl]-2-cyanoethyl-(N,N-diisopropyl)-phosphoramidite) (Glen Research, Sterling, Va., USA, Cat No. 10-4913-XX).

In some embodiments, a transposon nucleic acid can include an anchor site. In some embodiments, an anchor site can include sequences that can specifically bind to capture probes. In some embodiments, the anchor site comprises sequences that are complementary and/or substantially complementary to capture probes comprising nucleic acids. In some embodiments, an anchor site can include a ligand or receptor that binds a capture probe comprising a corresponding receptor or ligand. In other words, an anchor site and a capture probe can comprise a ligand/receptor pair. In some embodiments, a ligand or receptor can be associated with the anchor site of a transposon nucleic acid through a modified nucleotide. Examples of ligands and receptors include biotin or polyHis that can bind streptavidin or nickel, respectively. Other examples include, pairs of ligands and their receptors known in the art, for example, avidin-biotin, streptavidin-biotin, and derivatives of biotin, streptavidin, or avidin, including, but not limited to, 2-iminobiotin, desthiobiotin, NeutrAvidin (Molecular Probes, Eugene, Oreg.), CaptAvidin (Molecular Probes), and the like; binding proteins/peptides, including maltose-maltose binding protein (MBP), calcium-calcium binding protein/peptide (CBP); antigen-antibody, including epitope tags, including c-MYC, HA, VSV-G, HSV, V5, and FLAG Tag™, and their corresponding anti-epitope antibodies; haptens, for example, dinitrophenyl and digoxigenin, and their corresponding antibodies; aptamers and their corresponding targets; poly-His tags (e.g., penta-His and hexa-His) and their binding partners including corresponding immobilized metal ion affinity chromatography (IMAC) materials and anti-poly-His antibodies; fluorophores and anti-fluorophore antibodies; nucleic acid strands and their complementary strands; and the like.

In some embodiments, a transposon nucleic acid can include a reporter tag. Useful reporter tags include any of a variety of identifiable tags, labels, or groups known in the art. In certain embodiments, a reporter tag can emit a signal. Examples of signals include those that are fluorescent, chemiluminescent, bioluminescent, phosphorescent, radioactive, calorimetric, or electrochemiluminescent. Exemplary reporter tags include fluorophores, radioisotopes, chromogens, enzymes, antigens including epitope tags, semiconductor nanocrystals such as quantum dots, heavy metals, dyes, phosphorescent groups, chemiluminescent groups, electrochemical detection moieties, binding proteins, phosphors, rare earth chelates, transition metal chelates, near-infrared dyes, electrochemiluminescence labels, and mass spectrometer compatible reporter tags, such as mass tags, charge tags, and isotopes. More reporter tags that may be used with the methods and compositions described herein include spectral labels such as fluorescent dyes (e.g., fluorescein isothiocyanate, Texas red, rhodamine, and the like); radiolabels (e.g., 3H, 125I, 35S, 14C, 32P, 33P, etc.); enzymes (e.g., horseradish peroxidase, alkaline phosphatase etc.); spectral colorimetric labels such as colloidal gold or colored glass or plastic (e.g. polystyrene, polypropylene, latex, etc.); beads; magnetic labels; electrical labels; thermal labels; and mass tags.

In some embodiments, a transposon nucleic acid can include a barcode. In some embodiments, a population of transposomes can include transposon nucleic acids comprising the same barcode, one or more different barcodes, or each transposon nucleic acid can include a different barcode. In some embodiments, a barcode inserted into or attached to a target nucleic acid can be used to identify a target nucleic acid. In some embodiments, a barcode can be used to identify an insertion event into a target nucleic acid. In some embodiments, each transposome in a population of transposomes includes a transposon nucleic acid with a different barcode that can be used to identify an insertion site in the target nucleic acid. In some embodiments, a barcode can be used to identify the insertion site after fragmentation at a cleavage site, for example where a barcode straddles a cleavage site. Example barcodes, and methods for their preparation and use are set forth in Int. Pub. No. WO 2012/061832; US 2012/0208724, US 2012/0208705 and PCT/US2013/031023, each of which is incorporated herein by reference in its entirety. In some embodiments, barcodes inserted into a target nucleic acid can be useful as landmarks in subsequent alignment of fragmented sequences to obtain a sequence representation of the target nucleic acid. In some embodiments, fragments that include common barcodes can be identified as having overlapping sequences.

In some embodiments, a transposon nucleic acid can include two transposon elements that are linked to each other. A linker can be included in the insert such that a first transposon element is contiguous with a second transposon element. A particularly useful insert is one that forms a "looped" complex as set forth in Int. Pub. No. WO 2012/061832; US 2012/0208724, US 2012/0208705 and PCT/US2013/031023, each of which is incorporated herein by reference in its entirety. In such structures a single insert having contiguous transposon elements binds to two transposase subunits forming a "looped" complex. In some embodiments, the transposon nucleic acid can include a blocking group.

Substrates

Some embodiments of the methods and compositions provided herein include the use of a substrate having a surface. Useful substrates include, for example, solid supports and gels. In some embodiments, the surface binds nucleic acids. In some embodiments, the surface comprises a plurality of capture probes that bind nucleic acids to the surface via Watson-Crick complementarity. In some embodiments, the capture probes bind anchor tags. In some embodiments, the capture probes and anchor tags each comprise nucleic acids. In some embodiments, the capture probes and anchor tags comprise small molecule groups that specifically bind to one another, such a receptor or ligand as provided herein, for example, biotin, avidin, HisD, nickel, antibodies and antigens.

Substrates can be two- or three-dimensional and can be a planar surface (e.g., a glass slide) or can be shaped. Useful materials include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites. Suitable three-dimensional solid supports include, for example, spheres, microparticles, beads, membranes, slides, plates, micro machined chips, tubes (e.g., capillary tubes), microwells, microfluidic devices, channels, filters, or any other structure suitable for anchoring a nucleic acid or other capture probe. Solid supports can include planar micro arrays or matrices capable of having regions that include populations of nucleic acids or primers or other capture probes. Examples include nucleoside-derivatized CPG and polystyrene slides; derivatized magnetic slides; polystyrene grafted with polyethylene glycol, and the like.

Various compositions and associated methods of making and using those compositions can be used to attach, anchor or immobilize capture probes such as nucleic acids to a surface of a substrate. The attachment can be achieved through direct or indirect bonding to the surface. The bonding can be by covalent linkage (See e.g., Joos et al. (1997) Analytical Biochemistry, 247:96-101; Oroskar et al. (1996) Clin. Chem., 42:1547-1555; and Khandjian (1986) Mol. Bio. Rep., 11:107-11, each of which is incorporated herein by reference in its entirety). A preferred attachment is direct amine bonding of a terminal nucleotide of a nucleic acid to an epoxide integrated on the surface. The bonding also can be through non-covalent linkage. For example, biotin-streptavidin (Taylor et al. (1991) 1. Phys. D: Appl. Phys., 24:1443, which is incorporated herein by reference in its entirety) and digoxigenin with anti-digoxigenin (Smith et al., Science, 253: 1122 (1992), which is incorporated herein by reference in its entirety) are common tools for anchoring nucleic acids to surfaces. Attachment of a nucleic acid to a surface can be via an intermediate structure such as a bead, particle or gel. Attachment of nucleic acids to an array via a gel is exemplified by flow cells available commercially from Illumina Inc. (San Diego, CA) or described in US 2010/10111768; U.S. 2012/0270305; and WO 05/065814, each of which is incorporated herein by reference in its entirety.

In some embodiments, a substrate can have a continuous or monolithic surface. Thus, nucleic acid fragments can attach at spatially random locations wherein the distance between nearest neighbor fragments (or nearest neighbor clusters derived from the fragments) will be variable. The resulting arrays can have a variable or random spatial pattern of features. In some embodiments, a substrate used in a method set forth herein can include an array of capture probes that are present in a repeating pattern. In some such embodiments, the capture probes provide the locations to which nucleic acids can attach. In some embodiments, repeating patterns are hexagonal patterns, rectilinear patterns, grid patterns, patterns having reflective symmetry, patterns having rotational symmetry, or the like. The capture probes to which a modified nucleic acid attach can each have an area that is, or is smaller than, about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$, or a range defined by any two of the preceding values. Alternatively or additionally, each feature can have an area that is, or is larger than, about 100 nm$^2$, 250 nm$^2$, 500 nm$^2$, 1 µm$^2$, 2.5 µm$^2$, 5 µm$^2$, 10 µm$^2$, 100 µm$^2$, or 500 µm$^2$, or a range defined by any two of the preceding values. A cluster or colony of nucleic acids that result from amplification of fragments on an array (whether patterned or spatially random) can similarly have an area that is in a range above or between an upper and lower limit selected from those exemplified above.

In some embodiments, the density of features such as nucleic acids, capture probes, or captured nucleic acids on a surface can be at least 1000 features/mm$^2$, 10000 features/mm$^2$, 100000 features/mm$^2$, 1000000 features/mm$^2$, or any range between the foregoing values. In some embodiments, the density of features such as nucleic acids, capture probes, or captured nucleic acids on a surface can be at least 1000 features/µm$^2$, 10000 features/µm$^2$, 100000 features/µm$^2$, 1000,000 features/µm$^2$, 2000,000 features/µm$^2$, 3000,000 features/µm$^2$, 4000,000 features/µm$^2$, 5000,000 features/µm$^2$, 6000,000 features/µm$^2$, 7000,000 features/µm$^2$, 8000,000 features/µm$^2$, 9000,000 features/µm$^2$, 10,000,000 features/µm$^2$, 20,000,000 features/µm$^2$, 50,000,000 features/µm$^2$, 100,000,000 features/µm$^2$, or any range between the foregoing values.

Several commercially available sequencing platforms utilize substrates having wells that provide a barrier to the diffusion of detection reagents (e.g. pyrophosphate in platforms available from 454 LifeSciences (a subsidiary of Roche, Basel Switzerland) or protons in platforms available from Ion Torrent (a subsidiary of Life Technologies, Carlsbad California)) during sequence detection steps.

Some embodiments provided herein include amplifying portions of a target nucleic acid, modified nucleic acid, or fragments thereof. Any suitable amplification methodology known in the art can be used. In some embodiments, nucleic acid fragments are amplified in or on a substrate. For example, in some embodiments, the nucleic acid fragments are amplified using bridge amplification methodologies as exemplified by the disclosures of U.S. Pat. No. 5,641,658; U.S. Patent Publ. No. 2002/0055100; U.S. Pat. No. 7,115,400; U.S. Patent Publ. No. 2004/0096853; 10 U.S. Patent Publ. No. 2004/0002090; U.S. Patent Publ. No. 2007/0128624; and U.S. Patent Publ. No. 2008/0009420, each of which is incorporated herein by reference in its entirety.

Bridge amplification methods allow amplification products to be immobilized in or on a substrate in order to form arrays comprised of clusters (or "colonies") of immobilized nucleic acid molecules. Each cluster or colony on such an array is formed from a plurality of identical immobilized polynucleotide strands and a plurality of identical immobilized complementary polynucleotide strands. The arrays so-formed can be referred to herein as "clustered arrays". The products of solid-phase amplification reactions are so-called "bridged" structures when formed by annealed pairs of immobilized polynucleotide strands and immobilized complementary strands, both strands being immobilized on the solid support at the 5' end, preferably via a covalent attachment. Bridge amplification methodologies are examples of methods wherein an immobilized nucleic acid template is used to produce immobilized amplicons. Other suitable methodologies can also be used to produce immobilized amplicons from immobilized nucleic acid fragments produced according to the methods provided herein. For example one or more clusters or colonies can be formed via solid-phase PCR, solid-phase MDA, solid-phase RCA etc. whether one or both primers of each pair of amplification primers are immobilized.

It will be appreciated that any of the amplification methodologies described herein or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), for example, as described in U.S. Pat. No. 8,003,354, which is incorporated herein by reference in its entirety. The above amplification methods can be employed to amplify one or more nucleic acids of interest. For example, PCR, multiplex PCR, SDA, TMA, NASBA and the like can be utilized to amplify immobilized nucleic acid fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference in its entirety) and oligonucleotide ligation assay (OLA) (See e.g., U.S. Pat. Nos. 7,582,420, 5,185,243, 5,679,524 and 5,573,907; EP 0320308; EP 0336731; EP 0439182; WO 90101069; WO 89/12696; and WO 89109835, each of which is incorporated herein by reference in its entirety). It will be appreciated that these amplification methodologies can be designed to amplify immobilized nucleic acid fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate® assay (Illumina, Inc., San Diego, CA) or one or more assay set forth in U.S. Pat. Nos. 7,582,420 and 7,611,869, each of which is incorporated herein by reference in its entirety.

An isothermal amplification technique can be used in a method of the present disclosure. Exemplary isothermal amplification methods include, but are not limited to, Multiple Displacement Amplification (MDA) as exemplified by, for example, Dean et al., *Proc. Natl. Acad. Sci. USA* 99:5261-66 (2002) or isothermal strand displacement nucleic acid amplification as exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., *Molecular Methods for Virus Detection*, Academic Press, Inc., 1995; U.S. Pat. Nos. 5,455,166, and 5,130,238, and Walker et al., *Nucl. Acids Res.* 20:1691-96 (1992) or hyperbranched strand displacement amplification which is described in, for example Lage et al., *Genome Research* 13:294-307 (2003), each of which is incorporated herein by reference in its entirety.

Additional description of amplification reactions, conditions and components are set forth in U.S. Pat. No. 7,670,810, which is incorporated herein by reference in its entirety. Other useful isothermal amplification techniques include recombinase-facilitated amplification techniques such as those sold commercially as TwistAmp™ kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference in its entirety. Helicase dependent amplification can also be used, for example, as described in Xu et al. EMBO Rep 5:795-800 (2004), which is incorporated herein by reference in its entirety.

In some embodiments, it may be desirable to perform a re-seeding step. For example, modified nucleic acid fragments can be captured at locations within a region of a surface, replicated on one or more cycles of an amplification process, the original fragments and/or amplicons thereof can be released from the locations, the released nucleic acids can be captured at other locations in the same region, and the newly captured nucleic acids can be amplified. In a specific example, a single cycle of bridge amplification can be carried out for a fragment that was seeded on a surface and instead of washing away the original template fragment upon release from the surface, the template fragment can re-seed the surface at a new location that is proximal to the location where it had originally seeded. Subsequent rounds of bridge amplification will allow cluster growth at both the original seed location and at the re-seed location. Using such methods replicate colonies can be created at a region of a surface to provide technical replicates. Analysis of the sequences for the technical replicates can provide the benefit of error checking. For example, observed sequence variants that occur in only a subset of proximal clusters (that are identified as technical replicates) can be identified as amplification errors, whereas sequence variants that occur in all clusters that are identified as technical replicates for a particular fragment are more likely to be true variants.

Sequencing Nucleic Acids

Some embodiments of the methods described herein can include a step of sequencing fragments derived from a target nucleic acid. One example is sequencing-by-synthesis (SBS). In SBS, extension of a nucleic acid primer along a nucleic acid template (e.g. a fragment of a target nucleic acid or amplicon thereof) is monitored to determine the sequence of nucleotides in the template. The primer can hybridize to a priming site that is present in an insert as set forth above. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array using steps set forth herein can be subjected to an SBS technique under conditions where events occurring for different templates can be distinguished due to their location in the array.

In some embodiments, flow cells provide a convenient format for housing an array of nucleic acid fragments that is produced by the methods of the present disclosure and that is subjected to an SBS or other detection technique that involves repeated delivery of reagents in cycles. As used herein, "flow cell" includes a chamber having a surface across which one or more fluid reagents can be flowed. Generally, a flow cell will have an ingress opening and an egress opening to facilitate flow of fluid. Examples of flow cells and related fluidic systems and detection platforms that can be readily used in the methods of the present disclosure are described, for example, in Bentley et al., Nature 456: 53-59 (2008), WO 04/018497; U.S. Pat. No. 7,057,026; WO 91/06678; U.S. Pat. Nos. 7,329,492; 7,211,414; 7,315,019; 7,405,281, and US, each of which is incorporated herein by reference in its entirety. In particular embodiments, a gel is present on the interior surface of a flow cell and the gel provides a substrate to which one or more of the compositions set forth herein is attached and/or where one or more of the method steps set forth herein occur.

In some embodiments, to initiate a first SBS cycle, one or more labeled nucleotides, DNA polymerase, etc., can be flowed into/through a flow cell that houses an array of nucleic acid fragments. Those sites of an array where primer extension (e.g. via hybridization of the primer to a priming site located on an insert attached to a nucleic acid fragment) causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated "n" times to extend the primer by n nucleotides, thereby detecting a sequence of length "n". Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 071123744; U.S. Pat. Nos. 7,329,492; 7,211, 414; 7,315,019; 7,405,281, and US 2008/0108082, each of which is incorporated herein by reference in its entirety.

In some embodiments, other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference in its entirety). In pyrosequencing, released PPi can be detected by being converted to adenosine triphosphate (ATP) by ATP sulfurylase, and the level of ATP generated can be detected via luciferase produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to methods of the present disclosure are described, for example, in WO 2012058096, US 2005/0191698, U.S. Pat. Nos. 7,595,883, and 7,244,559, each of which is incorporated herein by reference in its entirety. Sequencing-by-ligation reactions are also useful including, for example, those described in Shendure et al. Science 309:1728-1732 (2005); U.S. Pat. Nos. 5,599,675; and 5,750,341, each of which is incorporated herein by reference in its entirety. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989110977, each of which is incorporated herein by reference in its entirety.

In some embodiments, sequencing-by-ligation and sequencing-by-hybridization procedures, target nucleic acid fragments (or amplicons thereof) that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and y-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); and Korlach et al. *Proc. Natl. Acad. Sci. USA* 105, 1176-1181 (2008), the disclosures of which are incorporated herein by reference in their entireties.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/10026082 AI; US 2009/10127589 AI; US 2010/10137143; or US 2010/10282617, each of which is incorporated herein by reference in its entirety.

In some embodiments, a sequencing step of the present methods can include a nanopore sequencing technique such as those described in Deamer & Akeson *Trends Biotechnol.* 18, 147-151 (2000); Deamer & Branton, *Acc. Chem. Res.* 35:817-825 (2002); and Li et al., *Nat. Mater.* 2:611-615 (2003), each of which is incorporated herein by reference in its entirety. In such embodiments, the target nucleic acid fragment passes through a nanopore. The nanopore can be a synthetic pore or biological membrane protein, such as a-hemolysin. As the target nucleic acid passes through the nanopore, each base-pair can be identified by measuring fluctuations in the electrical conductance of the pore. (U.S. Pat. No. 7,001,792; Soni & Meller *Clin. Chem.* 53, 1996-2001 (2007); Healy, *Nanomed.* 2:459-481 (2007); and Cockroft et al., 1. *Am. Chem. Soc.* 130:818-820 (2008), each of which is incorporated herein by reference in its entirety). In some embodiments, the location of individual nanopores is akin to a site or feature on the arrays exemplified herein. The proximity of nanopores to each other can be correlated with the proximity of fragment sequences they read, for example, to facilitate assembly of those fragments into the larger sequence from which they were derived.

In some embodiments, the sequencing steps described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface bound target nucleic acids, or fragments thereof, the target nucleic acids, or fragments, can be in an array format. In an array format, fragments of target nucleic acids can be typically coupled to a surface in a spatially distinguishable manner, for example, using attachment techniques set forth herein. The array can include a single copy of a target nucleic acid fragment at each site (also referred to as a feature) or multiple copies having the same sequence can be present at each site or feature. Multiple copies can be produced by amplification methods such as, bridge amplification or emulsion PCR.

Preparation and Sequencing Nucleic Acids

Some embodiments of the compositions and methods provided herein include preparing a sequencing library from a target nucleic acid. Some embodiments also include sequencing the prepared library. In some embodiments, a population of transposomes, each transposome comprising a transposase and a transposon nucleic acid is contacted with a target nucleic acid. The contacting can occur in or on a substrate, or alternatively, in solution. The transposome can comprise one-sided transposase activity such that the target nucleic acid is nicked at a plurality of sites and single transposon nucleic acids are attached to the nicked strands at one side of the nicked sites. In some embodiments, a primer can be hybridized to each of the attached transposon nucleic acids and extended to obtain a population of single-stranded modified nucleic acids. In some embodiments, the extended nucleic acids can be amplified. In some embodiments, the extended and/or amplified nucleic acids, namely, the modified nucleic acids, can be captured to a surface for sequencing. Some embodiments also include sequencing the captured nucleic acids.

FIG. 1 depicts an example embodiment in which a target nucleic acid is contacted with a population of transposomes comprising a transposon nucleic acid. The target nucleic is nicked at a plurality of sites, and the transposon nucleic acid is attached to one strand of the nicked target nucleic acid at one-side of the nick site. Primers hybridize to the attached transposon nucleic acids to provide a population of extended nucleic acids. In some embodiments, the extended nucleic acids can be amplified. In some embodiments, the extended nucleic acids provide templates for a sequencing library.

Figure 2:
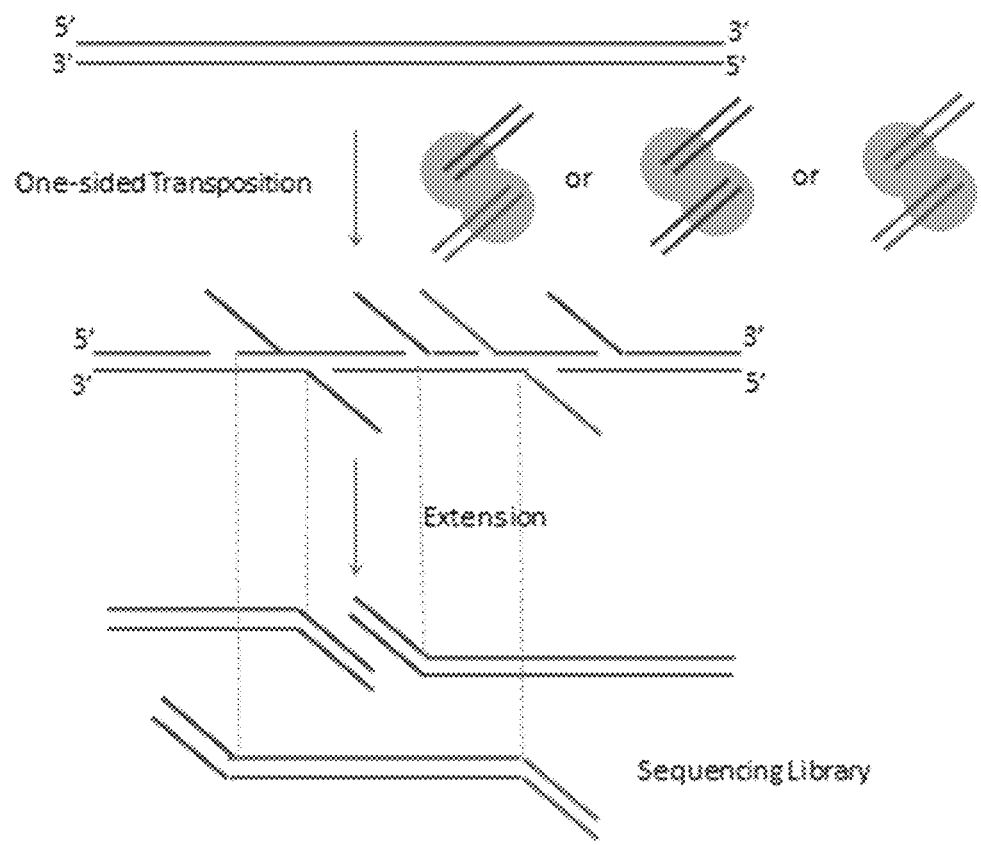
FIG. 2 depicts an example embodiment in which a population of transposomes comprises different transposon nucleic acids contacts a target nucleic acid and the different transposon nucleic acids are attached to a strand of the target nucleic acid at different nick sites.

In some embodiments, the transposome having one-sided transposase activity comprises a transposase having one-sided transposase activity. In some embodiments, the transposome comprises a blocked transposon nucleic acid. Transposomes useful with methods and compositions of preparing and sequencing libraries from a target nucleic are provided herein. In some embodiments, the transposon nucleic acid comprises an anchor site, a barcode, a sequencing primer site, an amplification primer site, and/or a reporter tag. FIG. 2 depicts an example embodiment in which a population of transposomes comprises different transposon nucleic acids contacts a target nucleic acid and the different transposon nucleic acids are attached to a strand of the target nucleic acid at different nick sites. In some embodiments, the different transposon nucleic acids can include different anchor sites, barcodes, sequencing primer sites, amplification primer sites, and/or reporter tags.

Figure 3:
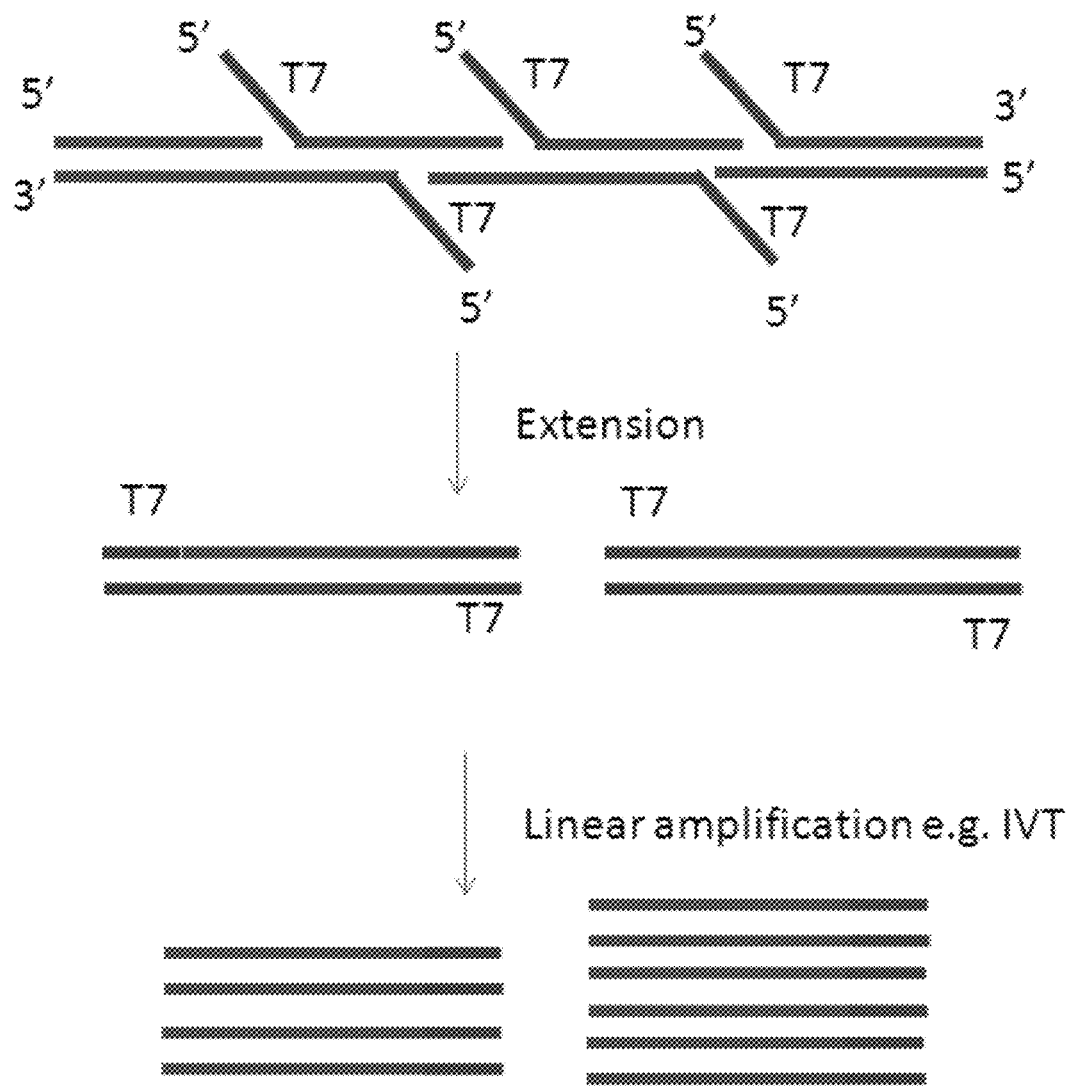
FIG. 3 depicts an example embodiment in which a modified target nucleic acid is amplified by linear amplification to obtain certain amplification products.

In some embodiments, extended nucleic acids are amplified. In some embodiments, the amplification is with tailed-amplification primers. A tailed primer can include additional end sequences such that the additional sequences are included in the amplification products. In some embodiments, amplification primers can include an anchor site, a sequencing primer site, an amplification primer site, and a reporter tag. FIG. 3 depicts an example embodiment in which a modified target nucleic acid is amplified by linear amplification to obtain certain amplification products.

Figure 4:
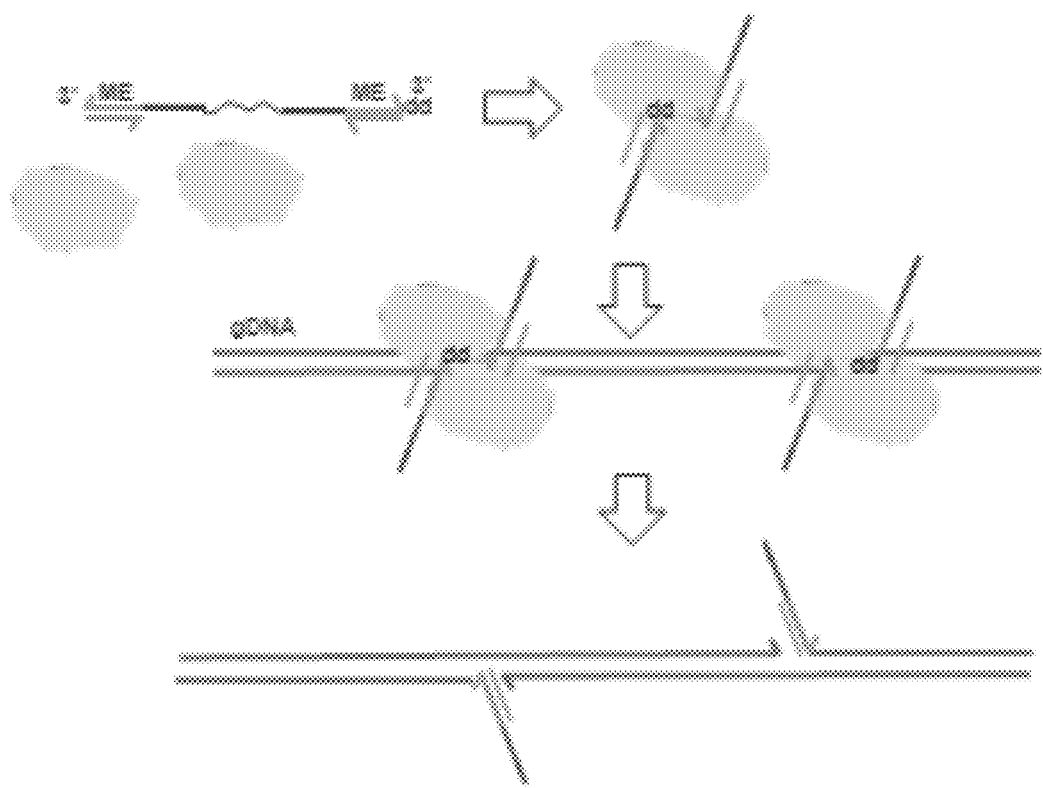
FIG. 4 depicts an example embodiment in which a transposome comprise a dimer transposase, and a transposon nucleic acid comprises two transposon elements comprising mosaic elements (ME) in which one of the ME is blocked with a dideoxy group at a 3' end.

FIG. 4 depicts an example embodiment in which a transposome comprise a dimer transposase, and a transposon nucleic acid comprises two transposon elements comprising mosaic elements (ME) in which one of the ME is blocked with a dideoxy group at a 3' end. In some embodiments, the transposon nucleic acid comprises a cleavable linker between the two transposon elements. The transposon nucleic acid can be cleaved, and the non-blocked fragment of the transposon nucleic acid can be attached to a strand of the nicked target nucleic acid at a nick site.

In some embodiments, the modified nucleic acids are captured on a surface. In some embodiments, the surface comprises a plurality of capture probes. In some embodiments, the capture probes comprise nucleic acids. In some embodiments, the capture probes specifically hybridize to the modified nucleic acids. In some embodiments the capture probes comprise an affinity moiety which binds to an affinity moiety of the modified nucleic acids. In some embodiments, the captured nucleic acids are amplified, for example, by bridge amplification. In some embodiments, the capture nucleic acids are sequenced on the surface.

Figure 5:
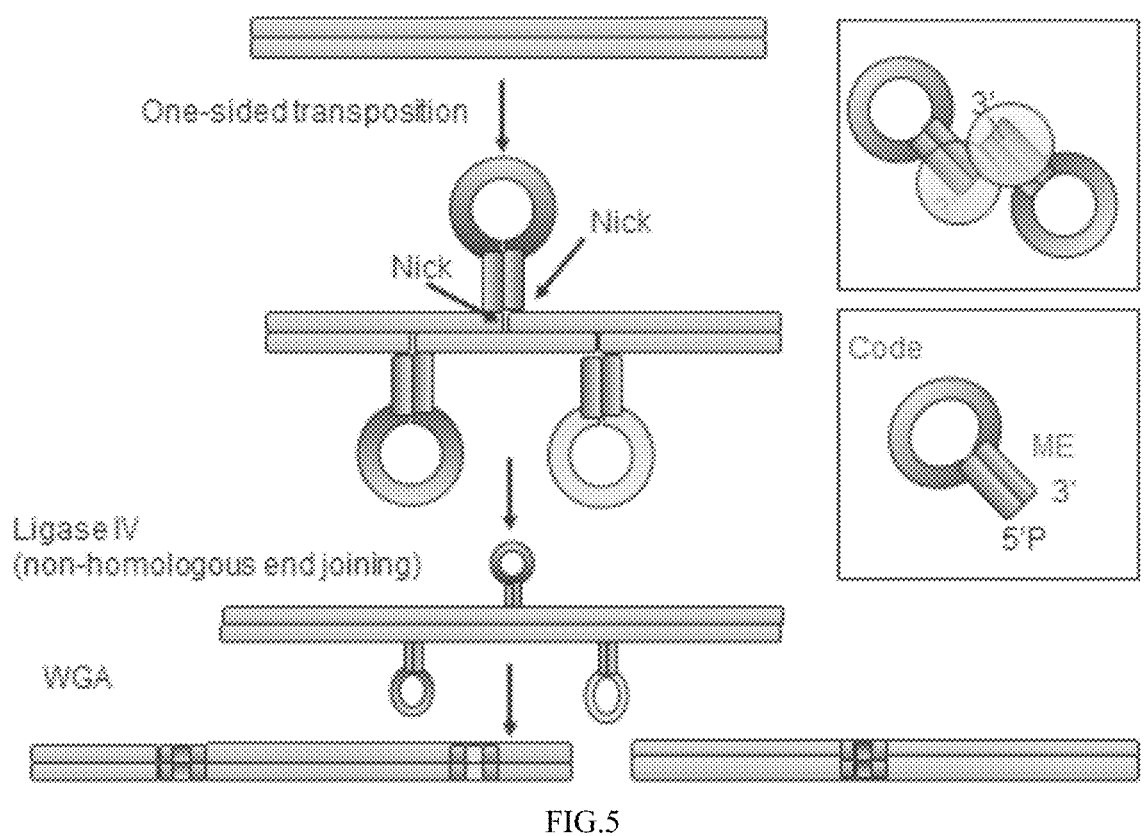
FIG. 5 depicts an example embodiment in which a population of transposomes comprising different barcodes contact a target nucleic acid; the transposon nucleic acids attach to one-side of the nick sites and the other non-attached end of the transposon nucleic acids is attached to the other side of the nick site by ligation; and the modified target nucleic acid is amplified by whole genome amplification (WGA).

Some embodiments of the methods and compositions provided herein also include preparing a sequencing library comprising barcodes. Some embodiments also include sequencing such libraries. In some embodiments, the barcodes provide landmarks useful in the alignment of sequenced fragments of the target nucleic acid. In some embodiments, transposon nucleic acids are inserted into single-strands of the target nucleic acid by one-side transposition and ligation. The modified target nucleic acid is amplified and fragments are sequenced. Overlapping fragments can include common insertions which are useful in the alignment of the sequenced fragments to generate a sequence representation of the target nucleic acid. FIG. 5 depicts an example embodiment in which a population of transposomes comprising different barcodes contact a target nucleic acid; the transposon nucleic acids attach to one-side of the nick sites and the other non-attached end of the transposon nucleic acids is attached to the other side of the nick site by ligation; and the modified target nucleic acid is amplified by whole genome amplification (WGA).

In some embodiments, a population of transposomes having one-sided transposase activity is contacted with a target nucleic acid. The transposomes comprise transposon nucleic acids which are inserted into strands of the target nucleic acid. Transposomes useful with such embodiments are described herein. In some embodiments, the transposon nucleic acids are inserted into single strands of the double-stranded target nucleic acid by contacting the target nucleic acid with the transposomes such that the target nucleic acid is nicked at a plurality of sites and single transposon nucleic acids are attached to the nicked strands at one side of the nicked sites, and ligating the attached single transposon nucleic acids to the nicked strands at the other side of the nicked sites. In some embodiments, the ligase can include a non-homologous end joining ligase. In some embodiments, the ligase can include ligase IV. In some embodiments the modified nucleic acid is amplified. In some embodiments, the modified nucleic acids are captured on a surface. In some embodiments, the modified nucleic acids are sequenced. In some embodiments, the sequences of the modified nucleic acids are aligned according to the presence of common barcodes in overlapping sequences. Some embodiments include a sequencing library comprising barcodes prepared by a method provided herein.

Obtaining Haplotype Information

Target nucleic acids such as genomic DNA can include more than a single haplotype. For example, human genomic DNA, contains two sets of DNA molecules, each set with a different combination of maternal and paternal sequences. Some embodiments provided herein are useful to obtain sequence information from fragments of a single nucleic acid molecule or copies thereof.

In some embodiments, the physical proximity of certain fragments on the substrate is maintained. In some embodiments, the sequences of fragments that have a closer proximity to one another in the sequence of the linear target nucleic acid have a closer physical proximity to one another on the surface compared to sequences of fragments that are less proximate from each other in the sequence of the linear target nucleic acid. The physical proximity of certain fragments can be retained by a variety of methods.

In some embodiments, one-sided transposition does not fragment a target nucleic acid. In some embodiments, a target nucleic acid can be contacted with transposomes having one-sided transposase activity to obtain a modified nucleic acid. In some embodiments, the modified nucleic acid can be contacted with a surface. In some embodiments, transposon nucleic acids include anchor tags such that modified sequences can be captured on a surface comprising capture probes. In some embodiments, the modified nucleic acid can be fragmented while in contact with the surface. In some embodiments, the modified nucleic acid can be fragmented at a location proximal to the surface. In some embodiments, the modified nucleic acid can be sequenced on the surface.

In some embodiments, methods to obtain haplotype information include comparing complementary sequences determined for proximal locations on the surface to identify sequence errors. In some embodiments, the relative proximity of any two fragment species on the surface can provide information useful for alignment of sequence information obtained from the two fragments. Specifically, the distance between clusters, derived from any two given fragments, on the surface can be positively correlated with the probability that the two clusters are from the same target polynucleotide molecule, as described in greater detail in WO 2012/025250, which is incorporated herein by reference in its entirety.

As an example, in some embodiments, fragments derived from a long nucleic acid molecule captured at the surface of a flow cell occur in a line across the surface of the flow cell (e.g. if the nucleic acid was stretched out prior to fragmentation or amplification) or in a cloud on the surface. Further, a physical map of the immobilized nucleic acid can then be generated. The physical map thus correlates the physical relationship of clusters after immobilized nucleic acid is amplified. Specifically, the physical map is used to calculate the probability that sequence data obtained from any two clusters are linked, as described in the incorporated materials of WO 2012/025250.

In some embodiments, the physical map is generated by imaging the surface to establish the location of the immobilized nucleic acid molecules across the surface. In some embodiments, the immobilized nucleic acid is imaged by adding an imaging agent to the solid support and detecting a signal from the imaging agent. In some embodiments, the imaging agent is a detectable label. Suitable detectable labels, include, but are not limited to, protons, haptens, radionuclides, enzymes, fluorescent labels, chemiluminescent labels, and/or chromogenic agents. For example, in some embodiments, the imaging agent is an intercalating dye or non-intercalating DNA binding agent. Any suitable intercalating dye or non-intercalating DNA binding agent as are known in the art can be used, including, but not limited to those set forth in U.S. 2012/0282617, which is incorporated herein by reference in its entirety.

In certain embodiments, a plurality of modified nucleic acid molecules is flowed onto a flow cell comprising a plurality of nano-channels. As used herein, the term nano-channel refers to a narrow channel into which a long linear nucleic acid molecule is stretched. In some embodiments, the number of strands is, or is no more than 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900 or 1000 individual long strands of nucleic acid, or a range defined by any two of the preceding values, that are stretched across each nano-channel. In some embodiments the individual nano-channels are separated by a physical barrier that prevents individual long strands of target nucleic acid from interacting with multiple nano-channels. In some embodiments, the solid support comprises, or comprises at least, 10, 50, 100, 200, 500, 1000, 3000, 5000, 10000, 30000, 50000, 80000 or 100000 nano-channels, or a range defined by any two of the preceding values.

In some embodiments, modified nucleic acids are cleaved once the nucleic acids have been stretched along the channel. The resulting fragments can be optionally amplified to form clusters along the surface of the channel. Contiguity mapping can then be performed, for example, by following the clusters down the length of one of these channels. As an example, a flow cell having 1000 or more nano-channels with mapped immobilized fragmentation products in the nano-channels can be used to sequence the genome of an organism with short 'positioned' reads. In some embodiments, mapped immobilized fragmentation products in the nano-channels can be used to resolve haplotypes. In some embodiments, mapped immobilized fragmentation products in the nano-channels can be used to resolve phasing issues.

In some embodiments, one-sided transposition is used to insert artificial DNA into gDNA. In one example artificial DNA is inserted into repeat regions of a genomic DNA (or other nucleic acid) to make repeat regions unique. The repeat regions can be analyzed, for example, by sequencing techniques, such as those set forth above, to count the number of repeats or to orient other sequences in the genomic DNA relative to the repeat regions. In another example, artificial DNA that is inserted by one-sided transposition makes the top and bottom strand of a double stranded nucleic acid different. Thus, the product of the insertion method can be analyzed, for example, by sequencing techniques, such as those set forth above, to discriminate one strand from the other. This can further allow independent assembly of top and bottom strand in a reconstruction of a genomic DNA (or other double stranded nucleic acid).

EXAMPLES

Example 1—Blocked Transposon Nucleic Acids

Figure 6:
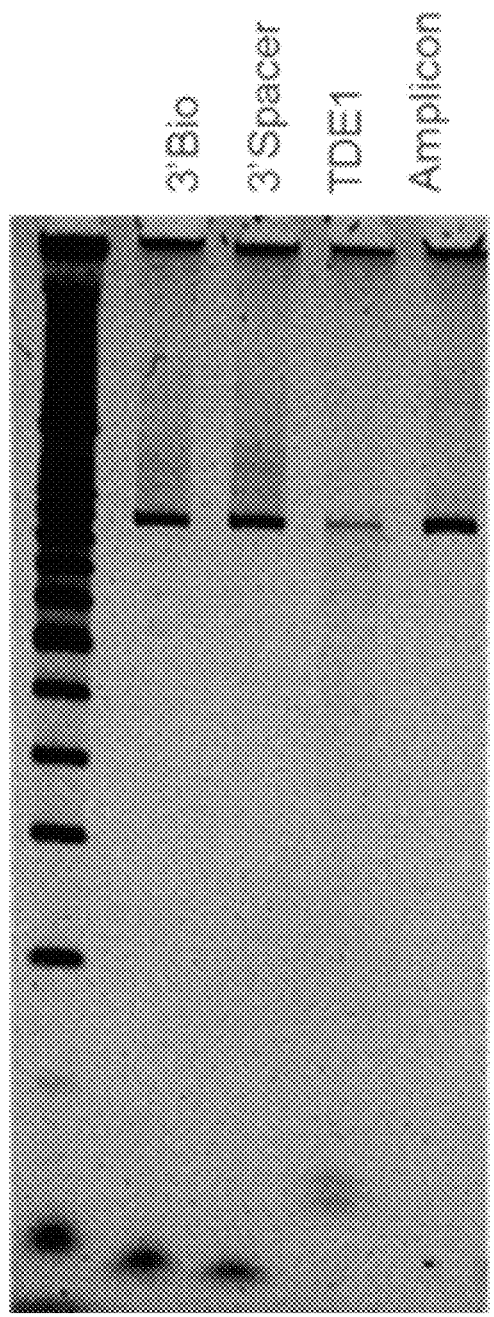
FIG. 6 depicts the results of treating genomic DNA was treated with no transposomes (Amplicon), or transposomes comprising transposase and (1) transposon nucleic acid blocked with a 3' biotin group (3' Bio); (2) transposon nucleic acid blocked with a 3' spacer group (3' Spacer); or (3) non-blocked transposon nucleic acid (TDE1).

Target DNA was treated with no transposomes (Amplicon), or transposomes comprising transposase and (1) transposon nucleic acid blocked with a 3' biotin group (3' Bio); (2) transposon nucleic acid blocked with a 3' spacer group (3' Spacer); or (3) non-blocked transposon nucleic acid (TDE1). FIG. 6 depicts the results in which transposition does not occur with transposomes comprising blocked transposon nucleic acids (3' Bio, and 3' Spacer).

Example 2—Model of Landmark Insertion and Assembly

Figure 7:
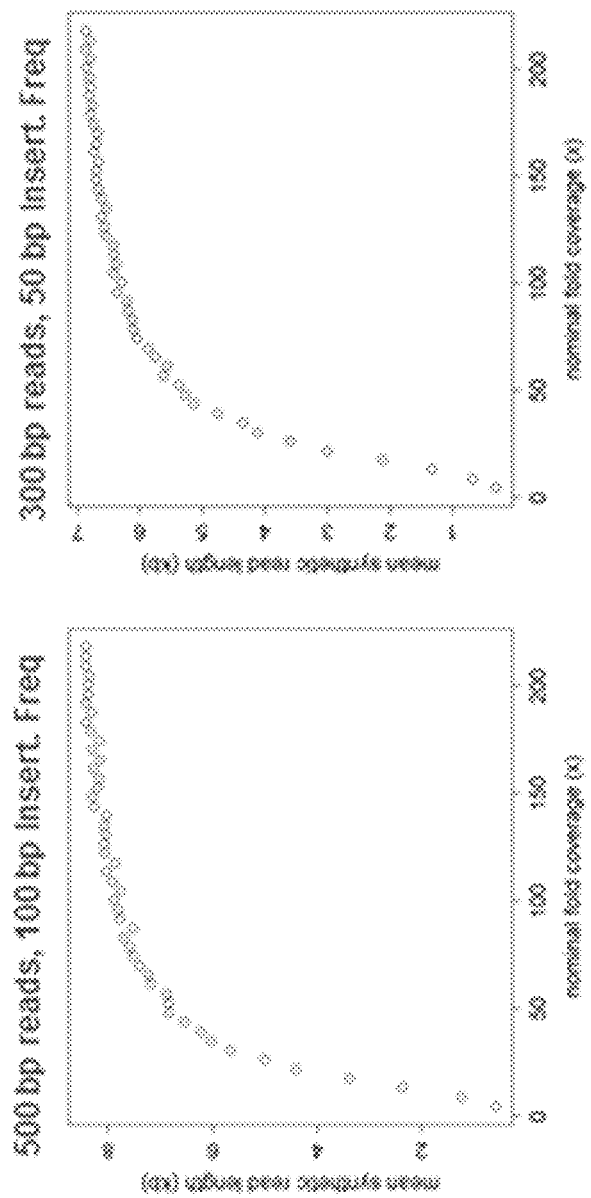
FIG. 7 shows graphs of nominal fold coverage, and mean synthetic read length for 500 bp reads with an insert frequency of 100 bp, and for 300 bp reads with an insert frequency of 50 bp.
Figure 8A:
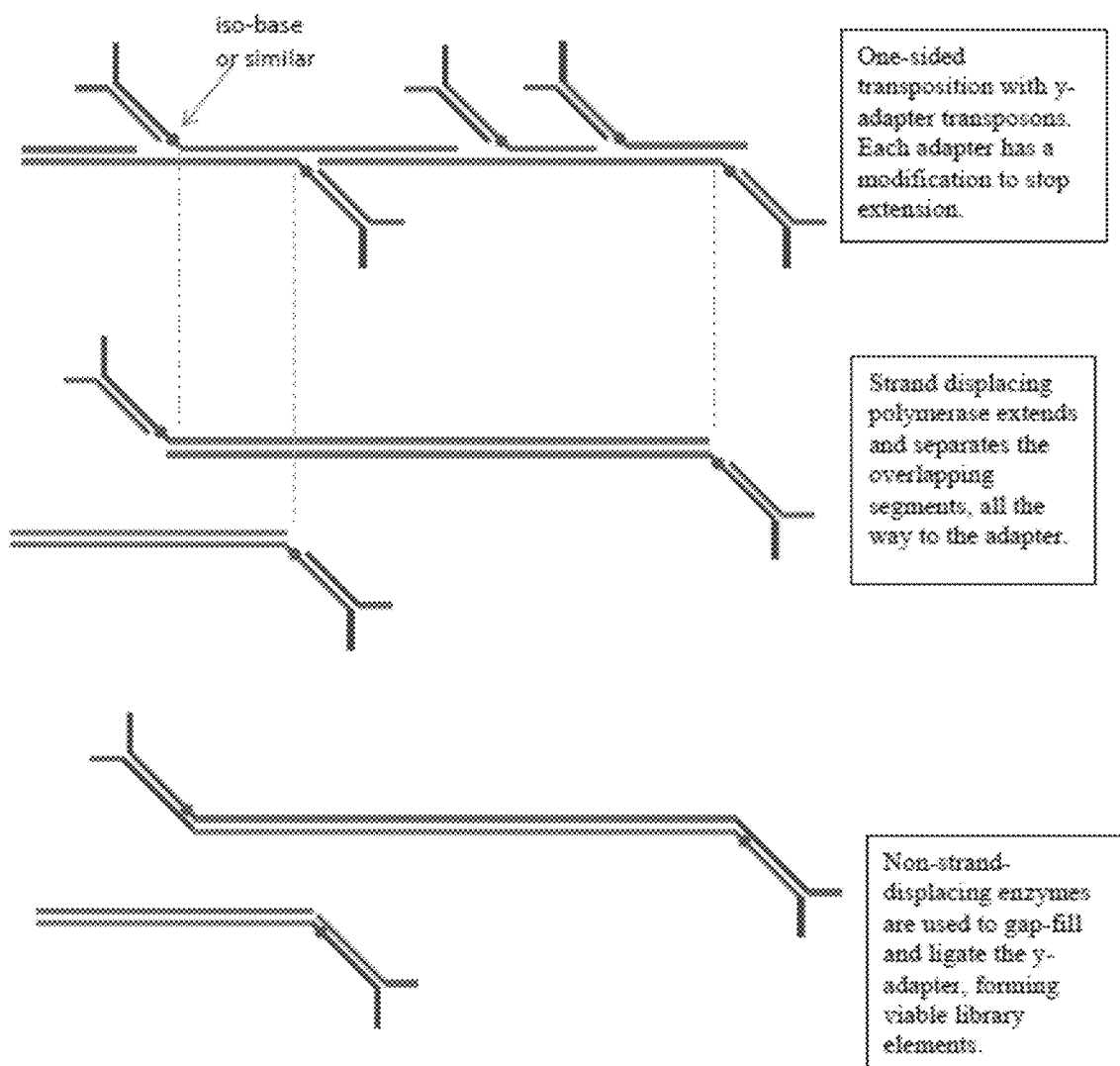
FIGS. 8A and 8B shows one-sided transposition with y-shaped adapter transposons.
Figure 8B:
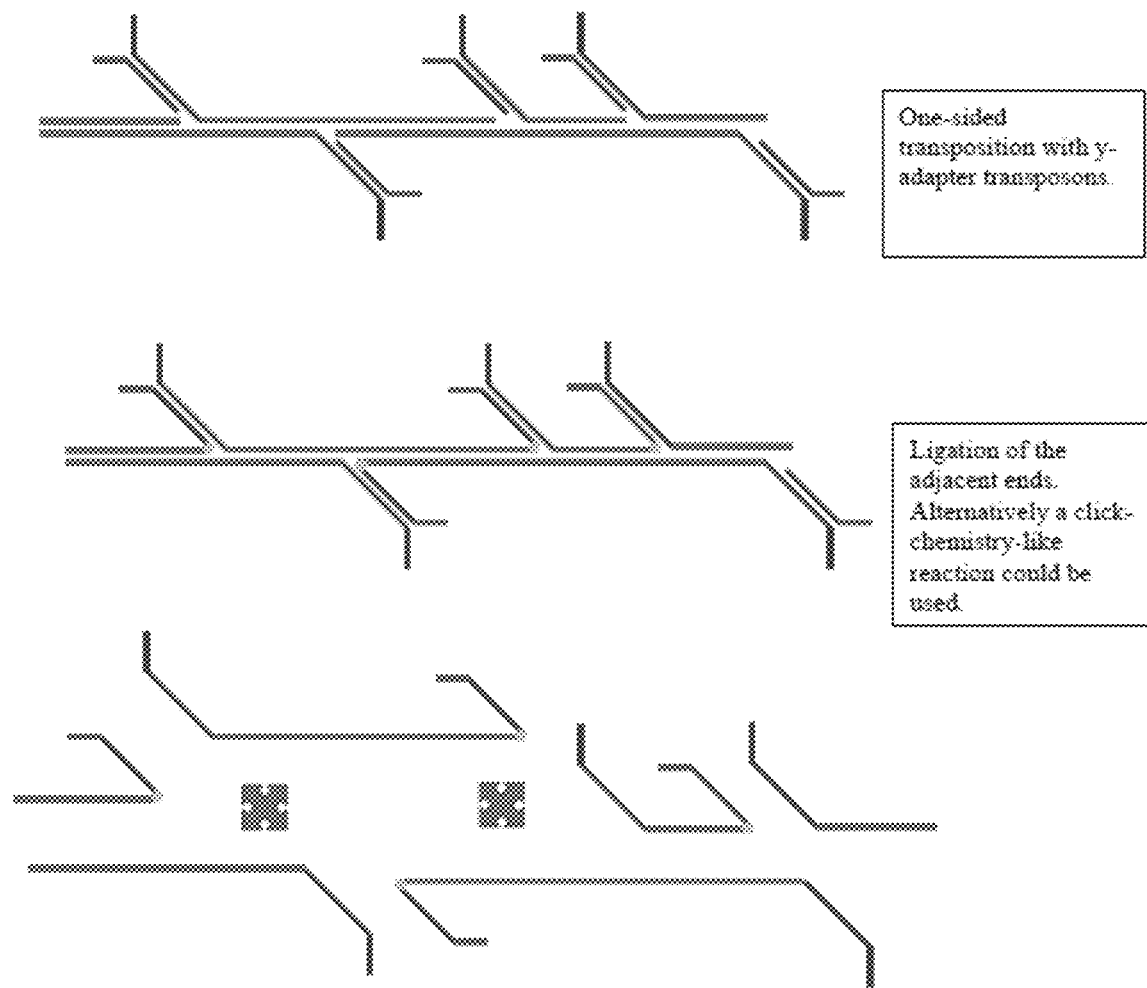

Landmarks comprising 12 bp random sequences were inserted in a target DNA. The DNA was sequenced and sequences fragments assembled de novo. FIG. 7 shows graphs of nominal fold coverage, and mean synthetic read length for 500 bp reads with an insert frequencies of 100 bp, and for 300 bp reads with an insert frequencies of 50 bp. It was demonstrated that 6-7 kb could be assembled de novo with 50× coverage.

Example 3—One-Sided Transposition with and without Glycerol

Figure 9:
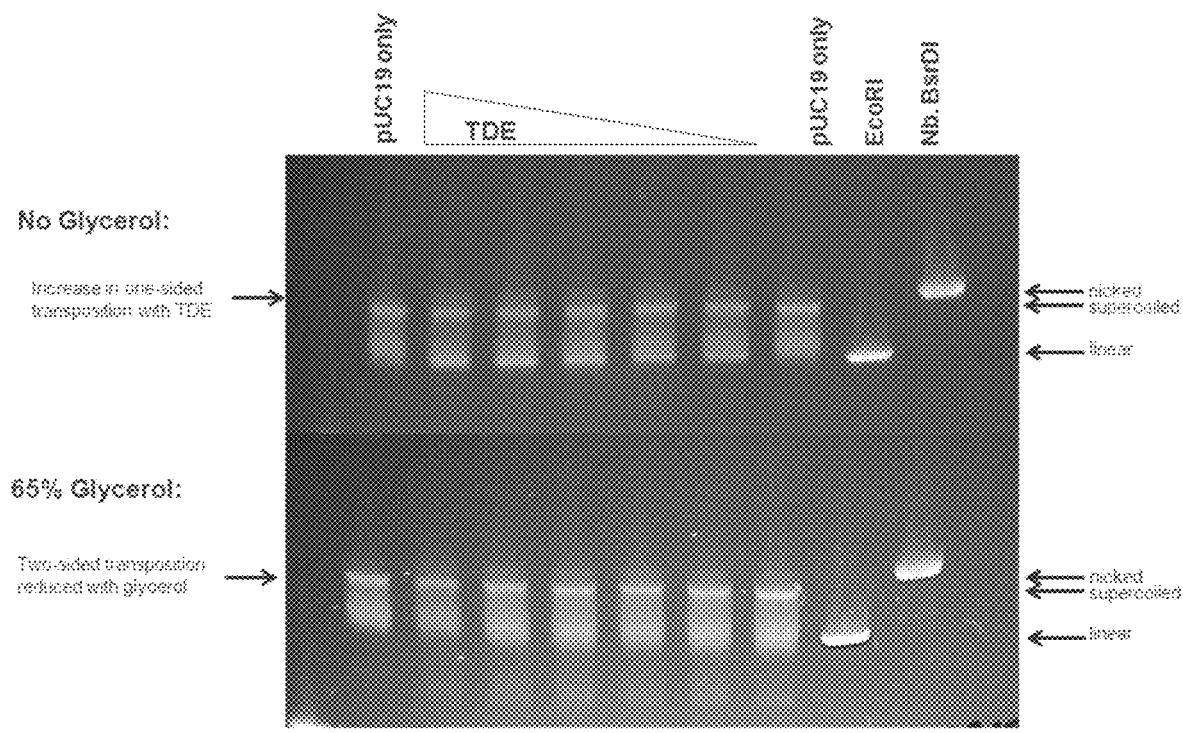
FIG. 9 shows a photograph of an agarose gel loaded with samples from one-sided transposition reactions.

Target DNA (pUC19) was incubated with transposomes and the DNA products were separated on a 1.2% gel. Ten samples were run: the first 5 samples including no glycerol and the second 5 samples including 65% glycerol. Each set of 5 samples was set up as a titration of different concentrations of the transposome. The transposome consisted of transposase and non-blocked transposon nucleic acid (TDE1). A photograph of the stained gel is shown in FIG. 9. The gel was also loaded with a controls for uncut pUC19 (pUC19 only), linearized pUC19 (EcoRI) and single strand nicked pUC19 (Nb. Bsr DI). As shown for the lanes of the gel that were loaded with the "no glycerol" samples, increasing concentration of TDE resulted in increase of one-sided transposition (i.e. nicked) products and two-sided transposition (i.e. linear) products. By comparison, the reactions that were run in the presence of 65% glycerol showed an increased amount of one-sided transposition product as TDE1 increased, but there was little to no two-sided transposition product increase in the presence of the increasing concentration of TDE1.

Example 4—Alterations in the Length of Transposon Nucleic Acids of the Transferred Strand Inhibits Transposition This example demonstrates that changes in the length of the transferred strand of a transposon by subtraction of one nucleotide (n−1) or addition of one nucleotide (n+1) reduces the efficiency of transposition.

Figure 10:
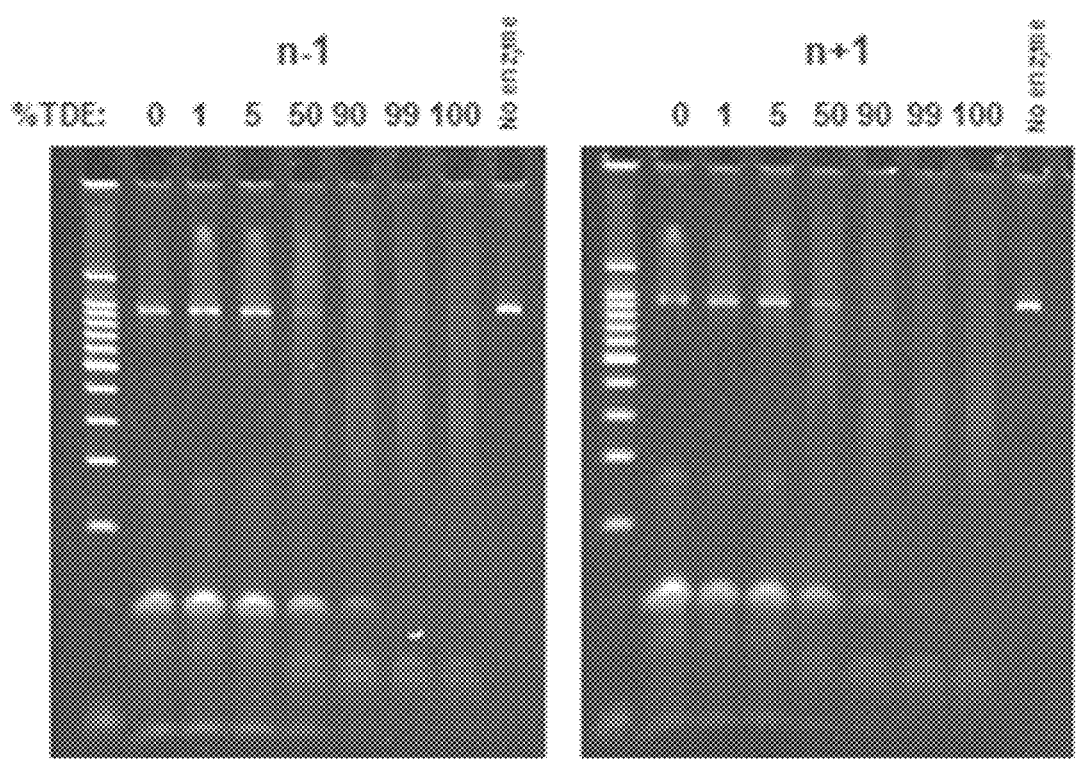
FIG. 10 shows photographs of agarose gels loaded with samples from transposition reactions run with n+1 and n−1 variants of a transposon.

Transposomes were formed with 3' n−1 and n+1 METS transposon and hybridized with 0, 1%, 5%, 50%, 90%, 99%, or 100% TDE1 overnight at room temperature. The resulting transposomes were then reacted overnight, at room temperature, with 1 kb amplicon, followed by treatment with SDS, and then separation on a TBE gel. FIG. 10 shows TBE gels loaded with the reaction products along with a molecular weight ladder and control sample having no transposase enzyme. Surprisingly, even with overnight incubation the majority of target DNA was still present in each sample, indicating that the n−1 and n+1 transposons had an inhibitory effect on transposition. Furthermore, the inhibitory effect correlated with increasing percentage of the n−1 and n+1 transposons.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure con-

What is claimed is:

1. A method of preparing a library of nucleic acids from a double-stranded target nucleic acid, comprising:
   (a) providing a plurality of transposomes, each transposome comprising a transposase and a transposon nucleic acid, wherein the transposon nucleic acid comprises a double-stranded y-shaped adapter, and the transposase comprises an activity to nick only one strand of the double-stranded target nucleic acid;
   (b) contacting the double-stranded target nucleic acid with the plurality of transposomes such that the double-stranded target nucleic acid is nicked at a plurality of sites and single transposon nucleic acids are attached to at least one of the nicked target nucleic acids to generate transposed nucleic acids; and
   (c) extending the transposed nucleic acids to generate a plurality of extended nucleic acids comprising overlapping sequences in a linear representation of a single target nucleic acid.

2. The method of claim 1, further comprising: (d) ligating a strand of the Y-shaped adapter to an extended strand of the extended nucleic acids.

3. The method of claim 1, wherein the y-shaped adapter comprises a blocking moiety.

4. The method of claim 1, wherein the plurality of transposomes is attached to a surface.

5. The method of claim 4, wherein the surface comprises a plurality of beads.

6. The method of claim 1, wherein step (b) further comprises removing the plurality of transposomes from the transposed nucleic acids.

7. The method of claim 1, wherein step (c) is performed in solution.

8. The method of claim 1, further comprising: amplifying the plurality of extended nucleic acids.

9. The method of claim 1, further comprising: sequencing the plurality of extended nucleic acids.

10. The method of claim 1, wherein the linear representation of the target nucleic acid sequence comprises a haplotype representation.

11. A method of preparing a library of nucleic acids from a double-stranded target nucleic acid, comprising:
    (a) providing a plurality of transposomes, each transposome comprising a transposase and a transposon nucleic acid, wherein the transposon nucleic acid comprises a double-stranded y-shaped adapter, and the transposase comprises an activity to nick only one strand of the double-stranded target nucleic acid;
    (b) contacting the double-stranded target nucleic acid with the plurality of transposomes such that the double-stranded target nucleic acid is nicked at a plurality of sites of the target nucleic acid, wherein each nicked site comprises a first end and a second end of a strand of the double-stranded target nucleic acid, and single transposon nucleic acids are attached to the first end of at least one of the nicked target nucleic acids to generate transposed nucleic acids; and
    (c) joining a strand of the Y-shaped adapters to the nicked strands of the double-stranded target nucleic acid at the second end of the nicked sites, to generate a plurality of modified nucleic acids which comprise overlapping sequences in a linear representation of a single target nucleic acid, thereby obtaining a library of nucleic acids.

12. The method of claim 11, further comprising (d) amplifying the modified nucleic acids.

13. The method of claim 11, wherein step (c) comprises: (i) ligating the strand of the Y-shaped adapters to the nicked strands at the other side of the nicked sites; or (ii) a click-chemistry reaction between the strand of the Y-shaped adapters to the nicked strands at the other side of the nicked sites.

14. The method of claim 11, wherein the plurality of transposomes is attached to a surface.

15. The method of claim 14, wherein the surface comprises a plurality of beads.

16. The method of claim 11, wherein step (b) further comprises removing the plurality of transposomes from the transposed nucleic acids.

17. The method of claim 11, wherein step (c) is performed in solution.

18. The method of claim 1, further comprising: sequencing the plurality of modified nucleic acids.

19. The method of claim 11, wherein the linear representation of the target nucleic acid sequence comprises a haplotype representation.

20. The method of claim 11, wherein the target nucleic acid comprises genomic DNA.

* * * * *